United States Patent
Takaoki et al.

(10) Patent No.: US 7,186,667 B2
(45) Date of Patent: *Mar. 6, 2007

(54) CATALYST COMPONENT AND CATALYST FOR ADDITION POLYMERIZATION, AND PROCESS FOR PRODUCING ADDITION POLYMER

(75) Inventors: Kazuo Takaoki, Albany, CA (US); Yoshiya Okado, Sodegaura (JP)

(73) Assignee: Sumitomo Chemical Company, Limited, Osaka (JP)

( * ) Notice: Subject to any disclaimer, the term of this patent is extended or adjusted under 35 U.S.C. 154(b) by 235 days.

This patent is subject to a terminal disclaimer.

(21) Appl. No.: 10/743,039

(22) Filed: Dec. 23, 2003

(65) Prior Publication Data

US 2004/0186009 A1    Sep. 23, 2004

(30) Foreign Application Priority Data

Dec. 6, 2002    (JP) .............................. 2002-376686

(51) Int. Cl.
*C08F 4/6392* (2006.01)
*C08F 4/642* (2006.01)
*B01J 31/22* (2006.01)

(52) U.S. Cl. .................. 502/111; 203/103; 203/128; 203/132; 203/152; 203/171; 203/172; 526/144; 526/160; 526/161

(58) Field of Classification Search ............... 502/103, 502/111, 152, 171, 172, 128, 132; 526/144, 526/160, 161

See application file for complete search history.

(56) References Cited

U.S. PATENT DOCUMENTS

2002/0143124 A1* 10/2002 Ogane ..................... 526/160

2003/0069127 A1    4/2003 Taboort et al.

FOREIGN PATENT DOCUMENTS

WO    WO02/051878 A1    7/2002

OTHER PUBLICATIONS

Jones et al., Inorg. Chem., vol. 32, pp. 5136-5144, (1993).
Whitmire et al., Inorg. Chem., vol. 39, pp. 85-97, (2000).

* cited by examiner

*Primary Examiner*—Caixia Lu
(74) *Attorney, Agent, or Firm*—Birch, Stewart, Kolasch & Birch, LLP

(57) ABSTRACT

A catalyst component obtained by a process comprising contacting (a), (b) and (c) described below, a catalyst for addition polymerization using the catalyst component, and a process for producing an addition polymer with the catalyst for addition polymerization:

(a) a compound represented by the chemical formula, $$BiL^1_r,$$

(b) a compound represented by the chemical formula, $$R^1_{s-1}T^1H, \text{ and}$$

(c) a compound represented by the chemical formula, $$R^2_{t-2}T^2H_2,$$

wherein r is a numeral corresponding to a valence of Bi; $L^1$ is a hydrogen atom, a halogen atom, a hydrocarbon group or a hydrocarbon oxy group; $T^1$ and $T^2$ independently represents a non-metallic atom of Group 15 or 16 of the periodic table; s represents a numeral corresponding to a valence of $T^1$; t represents a numeral corresponding to a valence of $T^2$; $R^1$ is an electron-withdrawing group or an electron-withdrawing group-containing group; and $R^2$ represents a hydrocarbon group.

16 Claims, No Drawings

CATALYST COMPONENT AND CATALYST FOR ADDITION POLYMERIZATION, AND PROCESS FOR PRODUCING ADDITION POLYMER

This Nonprovisional application claims priority under 35 U.S.C. § 119(a) on Patent Application No(s). 2002-376686 filed in Japan on Dec. 26, 2002, the entire contents of which are hereby incorporated by reference.

BACKGROUND OF THE INVENTION

1. Technical Field

The present invention relates to a catalyst component for addition polymerization, a catalyst for addition polymerization using the catalyst component, and a process for producing an addition polymer using the catalyst.

2. Description of Related Arts

Since olefin polymers such as polypropylene and polyethylene are excellent in mechanical properties and chemical resistance, and excellent in balance between those properties and economical efficiency, they have been widely used for various fields such as a packaging field. These olefin polymers have been conventionally produced by polymerizing an olefin using a conventional type solid catalyst (multi-site catalyst) which combines a solid catalyst component obtained by using a metal compound of Group IV such as titanium trichloride or titanium tetrachloride, with a metal compound of the Group 13 represented by an organoaluminum compound.

But, as a catalyst providing addition polymers having less in stickiness and more excellent in strength than those produced by the conventional catalyst, a so-called single site catalyst prepared by combining a catalyst component such as a metallocen complex or half metallocen complex with a co-catalyst component for activation such as an aluminoxane, and tri(n-butyl)ammonium tetrakis(pentafluorophenyl)borate, was proposed and with respect to the single site catalyst, improvements for using it in an industrial scale have been studied(e.g. JP 58-19309 A, U.S. Pat. No. 5,621,126, U.S. Pat. No. 5,153,157).

Further, recently, a compound prepared by contacting diethylzinc, pentafluorophenol and water, is developed as a co-catalyst component for activation, and a catalyst prepared by contacting said co-catalyst component with the metallocen complex or half metallocen complex, are proposed as a high activity catalyst(e.g. U.S. Pat. No. 6,586,356).

SUMMARY OF THE INVENTION

However, according to the inventor's studies, when olefins were addition-polymerized with the above-mentioned catalyst, olefin polymers thus obtained were not satisfactory in height of molecular weight. Under the above-situations, the present invention provides a catalyst component for addition polymerization which can produce an addition polymer of high molecular weight, a catalyst for addition polymerization which is made by using the catalyst component, and a process for producing an addition polymer using the catalyst for addition polymerization.

Namely, the present invention relates to a catlyst component obtained by a process comprising contacting (a), (b) and (c) described below, a catalyst for addition polymerization comprising the catalyst component, and a process for producing an addition polymer with the catalyst for addition polymerization:

(a) a compound represented by the chemical formula [1], $$BiL^1_r \qquad [1],$$

(b) a compound represented by the chemical formula [2], $$R^1_{s-1}T^1H \qquad [2], \text{ and}$$

(c) a compound represented by the chemical formula [3], $$R^2_{t-2}T^2H_2 \qquad [3],$$

wherein r is a numeral corresponding to a valence of Bi; $L^1$ is a hydrogen atom, a halogen atom, a hydrocarbon group or a hydrocarbon oxy group, and when more than one $L^1$ exist, they may be the same or different from one another; respective $T^1$ and $T^2$ independently represents a non-metallic atom of Group 15 or 16 of the periodic table; s represents a numeral corresponding to a valence of $T^1$; t represents a numeral corresponding to a valence of $T^2$; $R^1$ is an electron-withdrawing group or an electron-withdrawing group-containing group, and when more than one $R^1$ exists, they may be the same or different from one another; and $R^2$ represents a hydrocarbon group, and when more than one $R^2$ exists, they may be the same or different from one another.

Further, the present invention is illustrated in detail below.

DETAILED DESCRIPTION OF THE INVENTION

In the above formula [1], Bi is a bismuth atom, and r represents a numeral corresponding to a valence of Bi, and is 3 or 5, preferably 3.

$L^1$ in the above formula [1] represents a hydrogen atom, a halogen atom, a hydrocarbon group or a hydrocarbon oxy group, and when more than one $L^1$ exist, they may be the same or different from each other. Specific examples of the halogen atom include a fluorine atom, a chlorine atom, a bromine atom and an iodine atom. As the hydrocarbon group, an alkyl group, an aryl group or an aralkyl group is preferred. As the hydrocarbon oxy group, an alkoxy group or an aryloxy group is preferred.

Examples of the alkyl group include a methyl group, an ethyl group, a n-propyl group, an isopropyl group, a n-butyl group, a sec-butyl group, a tert-butyl group, an isobutyl group, a n-pentyl group, a neopentyl group, a n-hexyl group, a n-octyl group, an-decyl group, an-dodecyl group, an-pentadecyl group and a n-eicosyl group.

These alkyl groups may be substituted with a halogen atom such as a fluorine atom, a chlorine atom, a bromine atom or an iodine atom. Examples of the alkyl group substituted with the halogen atom include a fluoromethyl group, a difluoromethyl group, a trifluoromethyl group, a chloromethyl group, a dichloromethyl group, a trichloromethyl group, a bromomethyl group, a dibromomethyl group, a tribromomethyl group, an iodomethyl group, a diiodomethyl group, a triiodomethyl group, a fluoroethyl group, a difluoroethyl group, a trifluoroethyl group, a tetrafluoroethyl group, a pentafluoroethyl group, a chloroethyl group, a dichloroethyl group, a trichloroethyl group, a tetrachloroethyl group, a pentachloroethyl group, a bromoethyl group, a dibromoethyl group, a tribromoethyl group, a tetrabromoethyl group, a pentabromoethyl group, a perfluoropropyl group, a perfluorobutyl group, a perfluoropentyl group, a perfluorohexyl group, a perfluorooctyl group, a perfluorododecyl group, a perfluoropentadecyl group, a perfluoroeicosyl group, a perchloropropyl group, a perchlorobutyl group, a perchloropentyl group, perchlorohexyl group, a perchlorooctyl group, a perchlorododecyl group, a perchloropentadecyl group, a perchloroeicosyl group, a perbromopropyl group, a perbromobutyl group, a perbromopentyl group, a perbromohexyl group, a perbromooctyl group, a perbromododecyl group, a perbromopentadecyl group and a perbromoeicosyl group.

The alkyl group as $L^1$ is preferably an alkyl group having 1 to 20 carbon atoms, and more preferably a methyl group, an ethyl group, an isopropyl group, a n-butyl group, a tert-butyl group or an isobutyl group.

As the aryl group as $L^1$, examples thereof include a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, a n-propylphenyl group, an isopropylphenyl group, a n-butylphenyl group, a sec-butylphenyl group, a tert-butylphenyl group, an isobutylphenyl group, a n-pentylphenyl group, a neopentylphenyl group, a n-hexylphenyl group, a n-octylphenyl group, a n-decylphenyl group, a n-dodecylphenyl group, a n-tetradecylphenyl group, a naphthyl group and an anthracenyl group.

The aryl group is preferably an aryl group having 6 to 20 carbon atoms, and more preferably a phenyl group or a 2-, 3-, or 4-tolyl group.

Examples of the aralkyl group as $L^1$ include a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (3,5-dimethylphenyl)methyl group, a (2,3,4-timethylphenyl)methyl group, a (2,3,5-timethylphenyl)methyl group, a (2,3,6-timethylphenyl)methyl group, a (3,4,5-timethylphenyl)methyl group, a (2,4,6-timethylphenyl)methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl)methyl group, an (ethylphenyl)methyl group, a (n-propylphenyl)methyl group, an (isopropylphenyl)methyl group, a (n-butylphenyl)methyl group, a (sec-butylphenyl)methyl group, a (tert-butylphenyl)methyl group, a (n-pentylphenyl)methyl group, a (neopentylphenyl)methyl group, a (n-hexylphenyl)methyl group, a (n-octylphenyl)methyl group, a (n-decylphenyl)methyl group, a (tetradecylphenyl)methyl group, a naphthylmethyl group and an anthracenylmethyl group.

The aralkyl group as $L^1$ is preferably an aralkyl group having 7 to 20 carbon atoms, and more preferably a benzyl group.

Examples of the alkoxy group as $L^1$ include a methoxy group, an ethoxy group, a n-propoxy group, an isopropoxy group, a n-butoxy group, a sec-butoxy group, a tert-butoxy group, an isobutoxy group, a n-pentyloxy group, a neopentyloxy group, a tert-pentyloxy group, a n-hexyloxy group, a n-heptyloxy group, a n-octyloxy group, a n-decyloxy group, a n-dodecyloxy group, a n-pentadecyloxy group, a n-eicosyl oxy group.

The alkoxy group as $L^1$ is preferably an alkoxy group having 1 to 20 carbon atoms, and more preferably a methoxy group, an ethoxy group, an isopropoxy group, a tert-butoxy group, an isobutoxy group, a neopentoxy group or tert-pentyloxy group.

Specific examples of the aryloxy group as $L^1$ include a phenoxy group, a 2-tolyloxy group, a 3-tolyloxy group, a 4-tolyloxy group, a 2,3-xylyloxy group, a 2,4-xylylphenoxy group, a 2,5-xylyloxy group, a 2,6-xylyloxy group, a 3,4-xylyloxy group, a 3,5-xylyloxy group, a 2,3,4-trimethylphenoxy group, a2,3,5-trimethylphenoxy group, a 2,3,6-trimethylphenoxy group, a 2,4,6-trimethylphenoxy group, a 3,4,5-trimethylphenoxy group, a 2,3,4,5-tetramethylphenoxy group, a 2,3,4,6-tetramethylphenoxy group, 2,3,5,6-tetramethylphenoxy group, a pentamethylphenoxy group, an ethylphenoxy group, a n-propylphenoxy group, an isopropylphenoxy group, a n-butylphenoxy group, a sec-butylphenoxy group, a tert-butylphenoxy group, an isobutylphenoxy, n-pentylphenoxy, a neopentylphenoxy, n-hexylphenoxy group, a n-octylphenoxy group, a n-decylphenoxy group, a n-tetradecylphenoxy group, a naphthoxy group, an anthrathenoxy group and the like.

The aryloxy group is preferably an aryloxy group having 6 to 20 carbon atoms, and more preferably a phenoxy group.

These alkyl, aryl, aralkyl, alkoxy and aryloxy groups above-mentioned as $L^1$ may be respectively substituted with a halogen atom such as a fluorine atom, a chlorine atom, a bromine atom or an iodine atom, an alkoxy group such as a methoxy group or an ethoxy group, an aryloxy group such as a phenoxy group, or an aralkyloxy group such as a benzyloxy group.

As $L^1$ in the above formula [1], preferred is a halogen atom, an alkyl group, an aryl group, alkoxy group or an aryloxy group, more preferred is a halogen atom, aryl group, alkoxy group or aryloxy group, and particularly preferable is an aryl group.

$T^1$ in the above-mentioned formula [2] represents a non-metallic atom of the Group 15 or Group 16 of the Periodic Table of the Elements (Revised edition of IUPAC Inorganic Chemistry Nomenclature 1989). Specific examples of the non-metallic atom of Group 15 include a nitrogen atom and a phosphorous atom, and specific examples of the non-metallic atom of Group 16 include an oxygen atom and a sulfur atom. $T^1$ is preferably a nitrogen atom or an oxygen atom, and more preferably an oxygen atom. s in the formula [2] represents a numeral corresponding to a valence of $T^1$, and for example, when $T^1$ is a non-metallic atom of the Group 15, s is 3 and when $T^1$ is a non-metallic atom of the Group 16, s is 2.

$R^1$ in the formula [2] represents an electron-withdrawing group or a group containing an electron-withdrawing group, and when a plural number of $R^1$'s exist, they may be mutually the same or different. As an index of the electron-withdrawing property, the substituent constant σ of the Hammet's rule is known, and a functional group in which the substituent constant σ of the Hammet's rule is positive can be mentioned as an electron-withdrawing group.

Specific examples of the electron-withdrawing group include a fluorine atom, a chlorine atom, a bromine atom, an iodine atom, a cyano group, a nitro group, a carbonyl group, a sulfonyl group, and a phenyl group.

The groups containing an electron-withdrawing group preferably include halogenated hydrocarbon groups such as halogenated alkyl groups and halogenated aryl groups, cyanated hydrocarbon groups such as cyanated aryl groups, nitrated hydrocarbon groups such as a nitrated aryl groups, hydrocarbonoxy carbonyl groups such as alkoxycarbonyl groups, aralkyloxycarbonyl groups and aryloxycarbonyl groups, and an acyloxy group.

Specific examples of the halogenated alkyl group as $R^1$ include a fluoromethyl group, a chloromethyl group, a bromomethyl group, an iodomethyl group, a difluoromethyl group, a dichloromethyl group, a dibromomethyl group, a diiodomethyl group, a trifluoromethyl group, a trichloromethyl group, a tribromomethyl group, a triiodomethyl group, a 2,2,2-trifluoroethyl group, a 2,2,2-trichloroethyl group, a 2,2,2-tribromoethyl group, a 2,2,2-triiodoethyl group, a 2,2,3,3,3-pentafluoropropyl group, a 2,2,3,3,3-pentachloropropyl group, a 2,2,3,3,3-pentabromopropyl group, a 2,2,3,3,3-pentaiodopropyl group, a 2,2,2-trifluoro-1-trifluoromethylethyl group, a 2,2,2-trichloro-1-trichloromethylethyl group, a 2,2,2-tribromo-1-tribromomethylethyl group, a 2,2,2-triiodo-1-triiodomethylethyl group, a 1,1-bis(trifluoromethyl)-2,2,2-trifluoroethyl group, a 1,1-bis(trichloromethyl)-2,2,2-trichloroethyl group, a 1,1-bis(tribromomethyl)-2,2,2-tribromoethyl group, and a 1,1-bis(triiodomethyl)-2,2,2-triiodoethyl group.

Specific examples of the halogenated aryl group as $R^1$ include aryl groups in which a hydrogen atom of an aromatic ring in the group is substituted with a halogen such as a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2,6-difluorophenyl group, a 3,5-difluorophenyl group, a 3,4,5-trifluorophenyl group, a 2,6-dichlorophenyl group, a 3,5-dichlorophenyl group, a 2,6-dibromophenyl group, a 3,5-dibromophenyl group, a 2,6-diiodophenyl group, a 3,5-diiodophenyl group, a 2,4,6-trifluorophenyl group, a 2,4,6-trichlorophenyl group, a 2,4,6-tribromophenyl group, a 2,4,6-triiodophenyl group, a pentafluorophenyl group, a pentachlorophenyl group, a pentabromophenyl group, and a pentaiodophenyl group.

Further, specific examples of the (halogenated alkyl)aryl group include aryl groups substituted with a halogenated alkyl group such as 2-(trifluoromethyl)phenyl group, a 3-(trifluoromethyl)phenyl group, a 4-(trifluoromethyl)phenyl group, a 2,6-bis(trifluoromethyl)phenyl group, a 3,5-bis(trifluoromethyl)phenyl group, and a 2,4,6-tris(trifluoromethyl)phenyl group.

Specific examples of the cyanated aryl group include a 2-cyanophenyl group, a 3-cyanophenyl group and a 4-cyanophenyl group.

Specific examples of the nitrated aryl group include a 2-nitrophenyl group, a 3-nitrophenyl group and a 4-nitrophenyl group.

Specific examples of the alkoxycarbonyl group include a methoxycarbonyl group, an ethoxycarbonyl group, a n-propoxycarbonyl group, an isopropoxycarbonyl group and a trifluoromethoxycarbonyl group.

Specific examples of the aralkyloxycarbonyl group include a benzyloxycarbonyl group.

Specific examples of the aryloxycarbonyl group include a phenoxycarbonyl group and pentafluorophenoxycarbonyl group.

Specific examples of the acyloxycarbonyl group include a methycarbonyloxy group and ethylcarbonyloxy group.

$R^1$ is preferably a halogenated hydrocarbon group, more preferably a halogenated alkyl group or a halogenated aryl group, further preferably a fluoroalkyl group, a fluoroaryl group, a chloroalkyl group or a chloroaryl group, particularly preferably a fluoroalkyl group or a fluoroaryl group.

Furthermore preferable is a fluoromethyl group, a difluoromethyl group, a trifluoromethyl group, a 2,2,2-trifluoroethyl group, a 2,2,3,3,3-pentafluoropropyl group, a 2,2,2-trifluoro-1-trifluoromethylethyl group, a 1,1-bis(trifluoromethyl)-2,2,2-trifluoroethyl group, a 4-fluorophenyl group, a 2,6-difluorophenyl group, a 3,5-difluorophenyl group, a 2,4,6-trifluorophenyl group, a 3,4,5-trifluorophenyl group, a pentafluorophenyl group, and a trifluoromethyl group, a 2,2,2-trifluoro-1-trifluoromethylethyl group, a 1,1-bis(trifluoromethyl)-2,2,2-trifluoroethyl group, a 3,4,5-trifluorophenyl group, or a pentafluorophenyl group is most preferable.

$T^2$ in the above-mentioned formula [3] independently represents a non-metallic atom of Group 15 or Group 16 of the Periodic Table of the Elements (Revised edition of IUPAC Inorganic Chemistry Nomenclature 1989). Specific examples of the non-metallic atom of Group 15 include a nitrogen atom, a phosphorous atom and the like, and specific examples of the non-metallic atom of Group 16 include an oxygen atom, a sulfur atom and the like. $T^2$ is preferably a nitrogen atom or an oxygen atom, and more preferably an oxygen atom.

t in the above-mentioned formula [3] represents a numeral corresponding to a valence of $T^2$, and for example, when $T^2$ is a non-metallic atom of Group 15, t is 3 and when $T^2$ is a non-metallic atom of Group 16, t is 2.

$R^2$ represented in the formula [3] represents a hydrocarbon group or a halogenated hydrocarbon group, and when a plural number of $R^2$'s exist, they may be mutually the same or different each other. The hydrocarbon group in $R^2$ is preferably an alkyl group, aryl group or aralkyl group, and the same hydrocarbon groups as illustrated in the general formula [2] as $L^1$ and the same halogenated hydrocarbon groups as illustrated in the general-formula [2] as $R^1$ are exemplified.

$R^2$ is preferably a halogenated hydrocarbon group, more preferably a fluorinated hydrocarbon group.

Specific examples of the compound (a) include halogenated bismuths(III) such as bismuth(III)fluoride, bismuth(III)chloride, bismuth(III)bromide and bismuth(III)iodide; trialkyl bismuths such as trimethyl bismuth; triaryl bismuths such as triphenyl bismuth; trialkoxy bismuths such as trimethoxy bismuth, triethoxy bismuth, triisoprpoxy bismuth, tri(tert-butoxy) bismuth, triisobutoxy bismuth, trineopentyloxy bismuth and tri(tert-pentyloxy) bismuth; triaryloxy bismuths such as triphenoxy bismuth, tri(2-tolyloxy) bismuth, tri(3-tolyloxy) bismuth, tri(4-tolyloxy) bismuth, tri(2,3-xylyloxy) bismuth, tri(2,4-xylyloxy) bismuth, tri(2,5-xylyloxy) bismuth, tri(2,6-xylyloxy) bismuth, tri(3,4-xylyloxy) bismuth, tri(3,5-xylyloxy) bismuth, tri(2,3,4-trimethylphenoxy) bismuth, tri(2,3,5-trimethylphenoxy) bismuth, tri(2,3,6-trimethylphenoxy) bismuth, tri(2,4,6-trimethylphenoxy) bismuth, tri(3,4,5-trimethylphenoxy) bismuth, tri(2,3,4,5-tetramethylphenoxy) bismuth, tri(2,3,4,6-tetramethylphenoxy) bismuth, tri(2,3,5,6-tetramethylphenoxy) bismuth, tri(pentamethylphenoxy) bismuth, tri(ethylphenoxy) bismuth, tri(n-propylphenoxy) bismuth, tri(isopropylphenoxy) bismuth, tri(n-butylphenoxy) bismuth, tri(sec-butylphenoxy) bismuth, tri(tert-butylphenoxy) bismuth, tri(isobutylphenoxy) bismuth, tri(n-pentylphenoxy) bismuth, tri(neopentylphenoxy) bismuth, tri(n-hexylphenoxy) bismuth, tri(n-octylphenoxy) bismuth, tri(n-decylphenoxy) bismuth, tri(n-dodecylphenoxy) bismuth, tri(n-tetradecylethylphenoxy)bismuth, trinaphtyloxy bismuth and trianthracenyloxy bismuth; halogenated bismuths (V) such as bismuth(V)fluoride, bismuth(V)chloride, bismuth(V)bromide and bismuth(V)iodide; pentaalkyl bismuths such as pentamethyl bismuth; pentaalkoxy bismuths such as pentamethoxy bismuth and pentaethoxy bismuth; and pentaaryloxy bismuths such as pentaphenoxy bismuth.

Among these, the compound(a) preferably includes halogenated bismuths(III), trialkyl bismuths, triaryl bismuths, trialkoxy bismuths, triaryloxy bismuths, more preferably halogenated bismuths(III), triaryl bismuths, trialkoxy bismuths and triaryloxy bismuths, and particularly preferably triaryl bismuths such as triphenyl bismuth. When the the compound (b) is an amine, specific examples thereof include di(fluoromethyl)amine, di(chloromethyl)amine, di(bromomethyl)amine, di(iodomethyl)amine, bis(difluoromethyl)amine, bis(dichloromethyl)amine, bis(dibromomethyl)amine, bis(diiodomethyl)amine, bis(trifluoromethyl)amine, bis(trichloromethyl)amine, bis(tribromomethyl)amine, bis(triiodomethyl)amine, bis (2,2,2-trifluoroethyl) amine, bis(2,2,2-trichloroethyl)amine, bis(2,2,2-tribromoethyl)amine, bis(2,2,2-triiodoethyl)amine, bis(2,2,3,3,3-pentafluoropropyl)amine, bis(2,2,3,3,3-pentachloropropyl)amine, bis(2,2,3,3,3-pentabromopropyl)amine, bis(2,2,3,3,3-pentaiodopropyl)amine, bis(2,2,2-trifluoro-1-trifluoromethylethyl)amine, bis(2,2,2-trichloro-1-trichloromethylethyl)amine, bis(2,2,2-tribromo-1-tribromomethylethyl)amine, bis(2,2,2-triiodo-1-triiodomethylethyl)amine, bis(1,1-bis(trifluoromethyl)-2,2,2-trifluoroethyl)amine, bis(1,1-bis(trichloromethyl)-2,2,2-trichloroethyl)amine, bis(1,1-bis(tribromomethyl)-2,2,2-tribromoethyl)amine, bis(1,1-bis(triiodomethyl)-2,2,2-triiodoethyl)amine, bis(2-fluorophenyl)amine, bis(3-fluorophenyl)amine, bis(4-fluorophenyl)amine, bis(2-chlorophenyl)amine, bis(3-chlorophenyl)amine, bis(4-chlorophenyl)amine, bis(2-bromophenyl)amine, bis(3-bromophenyl)amine, bis(4-bromophenyl)amine, bis(2-iodophenyl)amine, bis(3-iodophenyl)amine, bis(4-iodophenyl)amine, bis(2,6-difluorophenyl)amine, bis(3,5-difluorophenyl)amine, bis(2,6-dichlorophenyl)amine, bis(3,5-dichlorophenyl)amine, bis(2,6-dibromophenyl)amine, bis(3,5-dibromophenyl)amine, bis(2,6-diiodophenyl)amine, bis(3,5-diiodophenyl)amine, bis(2,4,6-trifluorophenyl)amine, bis(2,4,6-trichlorophenyl)amine, bis(2,4,6-tribromophenyl)amine, bis(2,4,6-triiodophenyl)amine, bis(pentafluorophenyl)amine, bis(pentachlorophenyl)amine, bis(pentabromophenyl)amine, bis(pentaiodophenyl)amine, bis(2-(trifluoromethyl)phenyl)amine, bis(3-(trifluoromethyl)phenyl)amine, bis(4-(trifluoromethyl)phenyl)amine, bis(2,6-di(trifluoromethyl)phenyl)amine, bis(3,5-di(trifluoromethyl)phenyl)amine, bis(2,4,6-tri(trifluoromethyl)phenyl)amine, bis(2-cyanophenyl)amine, bis(3-cyanophenyl)amine, bis(4-cyanophenyl)amine, bis(2-nitrophenyl)amine, bis(3-nitrophenyl)amine and bis(4-nitrophenyl)amine.

Further, when the compound (b) is a phosphine, specific examples thereof include phosphine compounds in which a nitrogen atom is replaced with a phosphorus atom in the above-mentioned amine compounds.

When the compound (b) is an alcohol, specific examples thereof include fluoromethanol, chloromethanol, bromomethanol, iodomethanol, difluoromethanol, dichloromethanol, dibromomethanol, diiodomethanol, trifluoromethanol, trichloromethanol, tribromomethanol, triiodomethanol, 2,2,2-trifluoroethanol, 2,2,2-trichloroethanol, 2,2,2-tribromoethanol, 2,2,2-triiodoethanol, 2,2,3,3,3-pentafluoropropanol, 2,2,3,3,3-pentachloropropanol, 2,2,3,3,3-pentabromopropanol, 2,2,3,3,3-pentaiodopropanol, 2,2,2-trifluoro-1-trifluoromethylethanol, 2,2,2-trichloro-1-trichloromethylethanol, 2,2,2-tribromo-1-tribromomethylethanol, 2,2,2-triiodo-1-triiodomethylethanol, 1,1-bis(trifluoromethyl)-2,2,2-trifluoroethanol, 1,1-bis(trichloromethyl)-2,2,2-trichloroethanol, 1,1-bis(tribromomethyl)-2,2,2-tribromoethanol and 1,1-bis(triiodomethyl)-2,2,2-triiodoethanol.

Further, when the compound (b) is an thiol compound, specific examples thereof include thiol compounds in which an oxygen atom is replaced with a sulfur atom in the above-mentioned alcohol compounds, for example, compounds represented by replacing methanol, ethanol and propanol in the above-mentioned specific examples of alcohols with methanethiol, ethanethiol and propane thiol, respectively and the like.

When the compound (b) is a phenol, specific examples thereof include 2-fluorophenol, 3-fluorophenol, 4-fluorophenol, 2-chlorophenol, 3-chlorophenol, 4-chlorophenol, 2-bromophenol, 3-bromophenol, 4-bromophenol, 2-iodophenol, 3-iodophenol, 4-iodophenol, 2,6-difluorophenol, 3,5-difluorophenol, 2,6-dichlorophenol, 3,5-dichlorophenol, 2,6-dibromophenol, 3,5-dibromophenol, 2,6-diiodophenol, 3,5-diiodophenol, 2,4,6-trifluorophenol, 3,4,5-trifluorophenol, 2,4,6-trichlorophenol, 2,4,6-tribromophenol, 2,4,6-triiodophenol, pentafluorophenol, pentachlorophenol, pentabromophenol, pentaiodophenol, 2-(trifluoromethyl)phenol, 3-(trifluoromethyl)phenol, 4-(trifluoromethyl)phenol, 2,6-bis(trifluoromethyl)phenol, 3,5-bis(trifluoromethyl)phenol, 2-cyanophenol, 3-cyanophenol, 4-cyanophenol, 2-nitrophenol, 3-nitrophenol, 4-nitrophenol.

Further, when the compound (b) is a thiophenol compound, specific examples thereof include thiophenol compounds in which an oxygen atom is replaced with a sulfur atom in the above-mentioned phenol compounds.

When the compounds (b) is a carboxylic acid, specific examples thereof include 2-fluorobenzoic acid, 3-fluorobenzoic acid, 4-fluorobenzoic acid, 2,3-difluorobenzoic acid, 2,4-difluorobenzoic acid, 2,5-difluorobenzoic acid, 2,6-difluorobenzoic acid, 2,3,4-trifluorobenzoic acid, 2,3,5-trifluorobenzoic acid, 2,3,6-trifluorobenzoic acid, 2,4,5-trifluorobenzoic acid, 2,4,6-trifluorobenzoic acid, 2,3,4,5-tetrafluorobenzoic acid, 2,3,4,6-tetrafluorobenzoic acid, pentafluorobenzoic acid, fluoroacetic acid, difluoroacetic acid, trifluoroacetic acid, pentafluoropropanoic acid, heptafluorobutanoic acid and 1,1-bis(trifluoromethyl)-2,2,2-trifluoroehtanoic acid.

When the compounds (b) is a sulfonic acid, specific examples thereof include fluoromethanesulfonic acid, difluoromethanesulfonic acid, trifluoromethanesulfonic acid, pentafluoroethanesulfonic acid, heptafluoropropanesulfonic acid, 1,1-bis(trifluoromethyl)-2,2,2-trifluoroehtane sulfonic acid.

The compound (b) preferably includes bis(trifluoromethyl)amine, bis(2,2,2-trifluoromethyl)amine, bis(2,2,3,3,3-pentafluoropropyl)amine, bis(2,2,2-trifluoro-1-trifluoromethylethyl)amine, bis(l,1-bis(trifluoromethyl)-2,2,2-trifluoroethyl)amine and bis (pentafluorophenyl) amine as amines; trifluoromethanol, 2,2,2-trifluoroethanol, 2,2,3,3,3-pentafluoropropanol, 2,2,2-trifluoro-1-trifluoromethylethanol and 1,1-bis(trifluoromethyl)-2,2,2-trifluoroethanol as alcohols; 2-fluorophenol, 3-fluorophenol, 4-fluorophenol, 2,6-difluorophenol, 3,5-difluorophenol, 2,4,6-trifluorophenol, 3,4,5-trifluorophenol, pentafluorophenol, 2-(trifluoromethyl)phenol, 3-(trifluoromethyl)phenol, 4-(trifluoromethyl)phenol, 2,6-bis(trifluoromethyl)phenol, 3,5-bis(trifluoromethyl)phenol and 2,4,6-tris(trifluoromethyl)phenol as phenols; pentafluorobenzoic acid and trifluoroacetic acid as carboxylic acids; and trifluoromethanesulfonic acid as sulfonic acids.

Further, the compound (b) more preferably includes bis(trifluoromethyl)amine, bis(pentafluorophenyl) amine, trifluoromethanol, 2,2,2-trifluoro-1-trifluoromethylethanol, 1,1-bis(trifluoromethyl)-2,2,2-trifluoroethanol, 4-fluorophenol, 2,6-difluorophenol, 2,4,6-trifluorophenol, 3,4,5-trifluorophenol, pentafluorophenol, 4-(trifluoromethyl)phenol, 2,6-bis(trifluoromethyl)phenol and 2,4,6-tris(trifluoromethyl)phenol, and further preferably 3,4,5-trifluorophenol, pentafluorophenol and 1,1-bis(trifluoromethyl)-2,2,2-trifluoroethanol.

The compound (c) preferably includes water, hydrogen disulfides, and alkylamines, arylamines, aralkylamines halogenated alkylamines, halogenated arylamines and (halogenated alkyl)arylamines having up to 20 carbon atoms, and specific examples thereof include water, hydrogen disulfide, methylamine, ethylamine, n-propylamine, isopropylamine, n-butylamine, sec-butylamine, tert-butylamine, isobutyl amine, n-pentylamine, neopentylamine, isopentyl amine, n-hexylamine, n-octylamine, n-decyl amine, n-dodecyl amine, n-eicosylamine, allylamine, cyclopentadienylamine, aniline, 2-tolylamine, 3-tolylamine, 4-tolylamine, 2,3-xylylamine, 2,4-xylylamine, 2,5-xylylamine, 2,6-xylylamine, 3,4-xylylamine, 3,5-xylylamine, 2,3,4-trimethylaniline, 2,3,5-trimethylaniline, 2,3,6-trimethylaniline, 2,4,6-trimethylaniline, 3,4,5-trimethylaniline, 2,3,4,5-tetramethylaniline, 2,3,4,6-tetramethylaniline, 2,3,5,6-tetramethylaniline, pentamethylaniline, ethylaniline, n-propylaniline, isopropylaniline, n-butylaniline, sec-butylaniline, tert-butylaniline, n-pentylaniline, neopentylaniline, n-hexylaniline, n-octylaniline, n-decylaniline, n-dodecylaniline, n-tetradecylaniline, naphthylamine, anthracenylamine, benzylamine, (2-methylphenyl)methylamine, (3-methylphenyl)methylamine, (4-methylphenyl)methylamine, (2,3-dimethylphenyl)methylamine, (2,4-dimethylphenyl)methylamine, (2,5-dimethylphenyl)methylamine, (2,6-dimethylphenyl)methylamine, (3,4-dimethylphenyl)methylamine, (3,5-dimethylphenyl)methylamine, (2,3,4-trimethylphenyl)methylamine, (2,3,5-trimethylphenyl)methylamine, (2,3,6-trimethylphenyl)methylamine, (3,4,5-trimethylphenyl)methylamine, (2,4,6-trimethylphenyl)methylamine, (2,3,4,5-tetramethylphenyl)methylamine, (2,3,4,6-tetramethylphenyl)methylamine, (2,3,5,6-tetramethylphenyl)methylamine, (pentamethylphenyl)methylamine, (ethylphenyl)methylamine, (n-propylphenyl)methylamine, (isopropylphenyl)methylamine, (n-butylphenyl)methylamine, (sec-butylphenyl)methylamine, (tert-butylphenyl)methylamine, (n-pentylphenyl)methylamine, (neopentylphenyl)methylamine, (n-hexylphenyl)methylamine, (n-octylphenyl)methylamine, (n-decylphenyl)methylamine, (n-dodecylphenyl)methylamine, naphtylmethylamine, anthracenylmethylamine, fluoromethylamine, chloromethylamine, bromomethylamine, iodomethylamine, difluoromethylamine, dichloromethylamine, dibromomethylamine, diiodomethylamine, trifluoromethylamine, trichloromethylamine, tribromomethylamine, triiodomethylamine, 2,2,2-trifluoroethylamine, 2,2,2-trichloroethylamine, 2,2,2-tribromoethylamine, 2,2,2-triiodoethylamine, 2,2,3,3,3-pentafluoropropylamine, 2,2,3,3,3-pentachloropropylamine, 2,2,3,3,3-pentabromopropylamine, 2,2,3,3,3-pentaiodopropylamine, 2,2,2-trifluoro-1-trifluoromethylethylamine, 2,2,2-trichloro-1-trichloromethylethylamine, 2,2,2-tribromo-1-tribromomethylethylamine, 2,2,2-triiodo-1-triiodomethylethylamine, 1,1-bis(trifluoromethyl)-2,2,2-trifluoroethylamine, 1,1-bis(trichloromethyl)-2,2,2-trichloroethylamine, 1,1-bis(tribromomethyl)-2,2,2-tribromoethylamine, 1,1-bis(triiodomethyl)-2,2,2-triiodoethylamine, 2-fluoroaniline, 3-fluoroaniline, 4-fluoroaniline, 2-chloroaniline, 3-chloroaniline, 4-chloroaniline, 2-bromoaniline, 3-bromoaniline, 4-bromoaniline, 2-iodoaniline, 3-iodoaniline, 4-iodoaniline, 2,6-difluoroaniline, 3,5-difluoroaniline, 2,6-dichloroaniline, 3,5-dichloroaniline, 2,6-dibromoaniline, 3,5-dibromoaniline, 2,6-diiodoaniline, 3,5-diiodoaniline, 2,4,6-trifluoroaniline, 2,4,6-trichloroaniline, 2,4,6-tribromoaniline, 2,4,6-triiodoaniline, pentafluoroaniline, pentachloroaniline, pentabromoaniline, pentaiodoaniline, 2-(trifluoromethyl)aniline, 3-(trifluoromethyl)aniline, 4-(trifluoromethyl)aniline, 2,6-di(trifluoromethyl)aniline, 3,5-di(trifluoromethyl)aniline and 2,4,6-tri(trifluoromethyl)aniline.

Further, more preferable compounds (c) include water, hydrogen disulfide, methylamine, ethylamine, n-propylamine, isopropylamine, n-butylamine, sec-butylamine, tert-butylamine, isobutyl amine, n-octylamine, aniline, 2,6-xylylamine, 2,4,6-trimethylaniline, naphthylamine, anthracenylamine, benzylamine, trifluoromethylamine, pentafluoroethylamine, perfluoroproylamine, perfluorobutylamine, perfluoropentylamine, perfluorohexylamine, perfluorooctylamine, perfluorododecylamine, perfluoropentadecylamine, perfluoroeicosylamine, 2-fluoroaniline, 3-fluoroaniline, 4-fluoroaniline, 2,6-difluoroaniline, 3,5-difluoroaniline, 2,4,6-trifluoroaniline, pentafluoroaniline, 2-(trifluoromethyl)aniline, 3-(trifluoromethyl)aniline, 4-(trifluoromethyl)aniline, 2,6-bis(trifluoromethyl)aniline, 3,5-bis(trifluoromethyl)aniline or 2,4,6-tris(trifluoromethyl)aniline; in particular, preferably water, trifluoromethylamine, perfluorobutylamine, perfluorooctylamine, perfluoropentadecylamine, 2-fluoroaniline, 3-fluoroaniline, 4-fluoroaniline, 2,6-difluoroaniline, 3,5-difluoroaniline, 2,4,6-trifluoroaniline, pentafluoroaniline, 2-(trifluoromethyl)aniline, 3-(trifluoromethyl)aniline, 4-(trifluoromethyl)aniline, 2,6-bis(trifluoromethyl)aniline, 3,5-bis(trifluoromethyl)aniline and 2,4,6-tris(trifluoromethyl)aniline; and most preferably water and pentafluoroaniline.

The catalyst component of the present invention is a reaction product(herein-after, referred to as "compound [A]") obtained by a process which contains contacting the above-mentioned compounds (a), (b) and (c). The order of contacting the compounds (a), (b) and (c) is not specifically limited, and for example, the following order can be adopted.

① A method of contacting (c) after contacting (a) and (b).
② A method of contacting (b) after contacting (a) and (c).
③ A method of contacting (a) after contacting (b) and (c).

The contact order is preferably ① or ②. Namely, the compound [A] is preferably obtained by contacting (c) with a contact product obtained by contacting (a) and (b), or by contacting (b) with a contact product obtained by contacting (a) and (c).

Further, in the method of contactong (a), (b) and (c), after contacting (a) and (b) or (a) and (c), thus obtained reaction products may be purified, then the purified products may be contacted with the remained component. On the other hand, the reaction products may be contacted the remained component without said purification.

The contact treatment of the the above-mentioned compounds (a)–(c) is preferably carried out under an inert gas atmosphere. The treatment temperature is usually from −100° C. to 200° C., and preferably from −80° C. to 150° C. The treatment time is usually from 1 minute to 36 hours, and preferably from 10 minutes to 24 hours. Further, a solvent maybe used in the treatment, and these compounds may be directly contact-treated without using it. As the solvent used, there can be used any solvent selected from non-polar solvents such as an aliphatic hydrocarbon solvenst and aromatic hydrocarbon solvents, and polar solvents such as etheral solvents, which are inert to the the compounds (a), (b) and (c). Specific examples of thereof include butane, hexane, heptane, octane, 2,2,4-trimethylpentane, cyclohexane, benzene, toluene, xylene, dimethyl ether, diethyl ether, diisopropyl ether, di-n-butyl ether, methyl tert-butyl ether, anisole, 1,4-dioxane, 1,2-dimethoxyethane, bis(2-methoxyethyl) ether, tetrahydrofuran, tetrahydropyran.

The amounts used of the respective compounds in the preparation of the compound (A) are not specifically limited. But, from the view point of heightening of the catalytic activity, when the molar ratio of the amounts used of the respective compounds is defined as a molar ratio of (a):(b):(c)=1: y: z , y is preferably 0.7×r to 1.3×r, more preferably 0.8×r to 1.2×r, further preferably 0.9×r to 1.1×r (whrein r is a valence of Bi), z is preferably 0.1 to 2, more preferably 0.4 to 1.8, further preferably 0.6 to 1.6, particularly preferably 0.8 to 1.4, most preferably 0.9 to 1.3.

As a result of the contact treatment, at least one of (a), (b) and (c) which are raw materials, may remain as unreacted matters concerning the compounds.

Here, when the compounds (a), (b) and (c) are respectively triphenyl bismuth, pentafluorophenol and water, an embodiment for producing the compound (A) of the present invention is shown below.

A toluene solution containing pentafluorophenol in amount of three times by mole to triphenyl bismuth is added dropwise to a toluene solution of triphenyl bismuth, and the resulted mixture is stirred under a reflux condition for 10 minutes to 24 hours, then cooled to room temperature to precipitate a crystal. After the crystal is separated by filteration, and then dried, the crystal is dissolved with toluene, then water in an equimolar amount to a bismuth component in the toluene solution is added dropwise to the toluene solution, and then resulted mixture is stirred at 80° C. for one hour.

The catalyst component (A) of the present invention is useful as a co-catalyst for addition polymerization, particularly, for olefin polymerization.

Specific examples of the catalyst for addition polymerization of the present invention include a catalyst for addition polymerization obtained by a process comprising contacting the the catalyst component (A) with a metal compound (B) of the Group 3 to the Group 11 or lanthanide series (herein-after, sometimes referred to simply as "compound (B)"), and a catalyst for addition polymerization obtained by a process comprising contacting the compound (A),the compound (B) and an organoaluminum compound (herein-after, sometimes referred to simply as "compound (C)").

Next, the catalyst for addition polymerization is described in detail below.

As the compound (B) used for addition polymerization catalyst of the present invention, it is not specifically limited so far as it is a metal compound of the Group 3 to 13 or Lanthanide Series of the Periodic Table exhibiting an addition polymerization activity by using together with the compound(A), or compound(A) and the compound(C), as an activating co-catalyst component.

Examples of the compound(B) includes metal compounds indicated by the chemical formula [7] described below, μ-oxo type metal compounds thereof.

  [7]

(wherein $M^6$ is a metal atom of the Group 3 to Group 11 or Lanthanide Series of the Periodic Table of the Elements; $L^2$ is a group having a cyclopentadienyl type anion skeleton or a group containing a hetero-atom, a plurality of $L^2$ groups may be the same or different each other, and a plurality of $L^2$ groups may be optionally linked in direct, or through a group containing a carbon atom, a silicone atom, a nitrogen atom, an oxygen atom, a sulfur atom or a phosphorus atom; $X^8$ is a halogen atom or a hydrocarbon group excluding the group having a cyclopentadienyl type anion skeleton or a hydrocarbonoxy group, and a plurality of $X^8$ groups may be the same or different each other; "a" represents a numeral satisfying an expression of 0<a≦8; and "b" represents a numeral satisfying an expression of 0<b≦8.)

In the formula [7], $M^6$ is a metal atom of Group 3 to Group 11 or Lanthanide Series of the Periodic Table (IUPAC 1985). Specific examples thereof include a scandium atom, yttrium atom, titanium atom, zirconium atom, hafnium atom, vanadium atom, niobium atom, tantalum atom, chromium atom, iron atom, ruthenium atom, cobalt atom, rhodium atom, nickel atom, palladium atom, samarium atom and ytterbium.

As the metal compound, M is preferably a transition metal compound, more preferably a titanium atom, zirconium atom or hafnium atom.

A group having a cyclopentadienyl type anion skeleton as $L^2$ includes a cyclopentadienyl group, a substituted cyclopentadienyl group, an indenyl group, a substituted indenyl group, a fluorenyl group, a substituted fluorenyl group and the like. Examples thereof include an $η^5$-(substituted)cyclopentadienyl group, an $η^5$-(substituted)indenyl group, an $η^5$-(substituted) fluorenyl group and the like. Specific examples thereof include an $η^5$-cyclopentadienyl group, an $η^5$-methylcyclopentadienyl group, an $η^5$-tert-butylcyclopentadienyl group, an $η^5$-1,2-dimethylcyclopentadienyl group, an $η^5$-1,3-dimethylcyclopentadienyl group, an $η^5$-1-tert-butyl-2-methylcyclopentadienyl group, an $η^5$-1-tert-butyl-3-methylcyclopentadienyl group, an $η^5$-1-methyl-2-isopropylcyclopentadienyl group, an $η^5$-1-methyl-3-isopropylcyclopentadienyl group, an $η^5$-1,2,3-trimethylcyclopentadienyl group, an $η^5$-1,2,4-trimethylcyclopentadienyl group, an $η^5$-tetramethylcyclopentadienyl group, an $η^5$-pentamethylcyclopentadienyl group, an $η^5$-indenyl group, an $η^5$-4,5,6,7-tetrahydroindenyl group, an $η^5$-2-methylindenyl group, an $η^5$-3-methylindenyl group, an $η^5$-4-methylindenyl group, an $η^5$-5-methylindenyl group, an $η^5$-6-methylindenyl group, an η5-7-methylindenyl group, an $η^5$-2-tert-butylindenyl group, an $η^5$-3-tert-butylindenyl group, an $η^5$-4-tert-butylindenyl group, an $η^5$-5-tert-butylindenyl group, an $η^5$-6-tert-butylindenyl group, an $η^5$-7-tert-butylindenyl group, an $η^5$-2,3-dimethylindenyl group, an $η^5$-4,7-dimethylindenyl group, an $η^5$-2,4,7-trimethylindenyl group, an $η^5$-2-methyl-4-isopropylindenyl group, an $η^5$-4,5-benzindenyl group, an $η^5$-2-methyl-4,5-benzindenyl group, an $η^5$-4-phenylindenyl group, an $η^5$-2-methyl-5-phenylindenyl group, an $η^5$-2-methyl-4-phenylindenyl group, an $η^5$-2-methyl-4-naphthylindenyl group, an $η^5$-fluorenyl group, an $η^5$-2,7-dimethylfluorenyl group, an $η^5$-2,7-di-tert-butylfluorenyl group, and substitution products thereof, etc.

The hetero-atom in the group containing a hetero-atom includes an oxygen atom, a sulfur atom, a nitrogen atom, a phosphorus atom and the like, and examples thereof include an alkoxy group, an aryloxy group, a thioalkoxy group, a thioaryloxy group, an alkylamino group, an arylamino group, an alkylphosphino group, an arylphosphino group, or an aromatic or aliphatic heterocyclic group having an oxygen atom, a sulfur atom, a nitrogen atom and/or a phosphorus atom in the ring, and a chelating ligand.

Specific examples of the group containing a hetero-atom include a methoxy group, an ethoxy group, a n- or iso-propoxy group, a n-, sec-, iso- or tert-butoxy group, a phenoxy group, a 2-methylphenoxy group, a 2,6-dimethylphenoxy group, a 2,4,6-trimethylphenoxy group, a 2-ethylphenoxy group, a 4-n-propylphenoxy group, a 2-isopropylphenoxy group, a 2,6-diisopropylphenoxy group, a 4-sec-butylphenoxy group, a 4-tert-butylphenoxy group, a 2,6-disec-butylphenoxy group, a 4-tert-butyl-4-methylphenoxy group, a 2,6-di-tert-butylphenoxy group, a 4-methoxyphenoxy group, a 2,6-dimethoxyphenoxy group, a 3,5-dimethoxyphenoxy group, a 2-chlorophenoxy group, a 4-nitrosophenoxy group, a 4-nitrophenoxy group, a 2-aminophenoxy group, a 3-aminophenoxy group, a 4-aminothiophenoxy group, a 2,3,6-trichlorophenoxy group, a 2,4,6-trifluorophenoxy group, a thiomethoxy group, a dimethylamino group, a diethylamino group, a di-n- or isopropylamino group, a diphenylamino group, an isopropylamino group, a tert-butylamino group, a pyrrolyl group, a dimethylphosphino group, a2-(2-oxy-1-propyl)phenoxy group, a catecholato group, a 2-hydoroxyphenoxy group, a resorcinolate group, a 3-hydoroxyphenoxy group, 4-isopropylcatechol, 3-methoxycatechol, a 1,8-dihydroxynahpthyl group, a 1,2-dihydroxynahpthyl group, a 2,2'-biphenyldiol group, a 1,1'-bi-2-naphthol group, a 2,2'-dihydroxy-6,6'-dimethylbiphenyl group, a 4,4',6,6'-tetra-tert-butyl-2,2'-methylenediphenoxy group, a 4,4',6,6'-tetramethyl-2,2'-isobutylidenediphenoxy group and the like.

Further, the hetero atom-containing group also includes a group represented by the formula[8]:

(wherein $R^3$ represents a hydrogen atom, halogen atom or hydrocarbon group, R groups may be the same or different, and two of them may be bonded mutually and may form a ring.)

Specific Examples of $R^3$ in the above-mentioned formula [8] include a hydrogen atom, fluorine atom, chlorine atom, bromine atom, iodine atom, methyl group, ethyl group, n-propyl group, isopropyl group, n-butyl group, tert-butyl group, cyclohexyl group, phenyl group, 1-naphtyl group, benzyl group and the like, but are not limited thereto.

Further, the hetero atom-containing group also includes a group represented by the formula [9]:

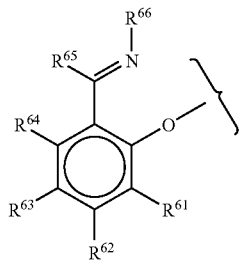

[9]

(wherein respective $R^{61}$–$R^{66}$ groups independently represent a hydrogen atom, halogen atom, hydrocarbon group, halogenated hydrocarbon group, hydrocarbon oxy group, silyl group or amino group, they may be the same or different, and two or more of them may be bonded mutually and may form a ring.)

Specific Examples of R in the general formula [9] include a hydrogen atom, fluorine atom, chlorine atom, bromine atom, iodine atom, phenyl group, 1-naphtyl group, 2-naphtyl group, tert-butyl group, 2,6-dimethylphenyl group, 2-fluorenyl group, 2-methylphenyl group, 4-trifluoromethylphenyl group, 4-methoxyphenyl group, 4-pyridyl group, cyclohexyl group, 2-isopropylphenyl group, benzyl group, methyl group, triethylsilyl group, diphenylmethylsilyl group, 1-methy-1-phenylethyl group, 1,1-dimethyl propyl group, 2-chlorophenyl group and the like, but are not limited thereto.

Further, the chelating ligand means a ligand having a plural number of coordinating positions, and specific examples thereof include an acetylacetonate, diimine, oxazoline, bisoxazoline, terpyridine, acylhydrazone, diethylenetriamine, triethylenetetramine, porphyrin, crown ether, cryptate and the like.

The mutual groups having the cyclopentadienyl type anion skeleton, the group having a cyclopentadienyl type anion skeleton and the group containing a hetero-atom, or the mutual groups containing a hetero-atom may be directly linked, or maybe linked through a group containing a carbon atom, a silicon atom, a nitrogen atom, an oxygen atom, a sulfur atom or a phosphorus atom, respectively. Examples of the group include alkylene groups such as an ethylene group and a propylene group, substituted alkylene groups such as a dimethylmethylene group and a diphenylmethylene group, or a silylene group, substituted silylene groups such as a dimethylsilylene group, a diphenylsilylene group and a tetramethyldisilylene group, or hetero-atoms such as a nitrogen atom, an oxygen atom, a sulfur atom and/or a phosphorus atom, etc.

$X^8$ in the formula [7] is a halogen atom, a hydrocarbon group excluding the group having a cyclopentadienyl type anion skeleton or a hydrocarbon oxy group. Specific examples of $X^8$ include a halogen atom such as a fluorine atom, chlorine atom, bromine atom and iodine atom, and hydrocarbon group such as an alkyl group, an aralkyl group, an aryl group and an alkenyl group.

The alkyl group as $X^8$, includes, for example, a methyl group, an ethyl group, a n-propyl group, an isopropyl group, a n-butyl group, a sec-butyl group, a tert-butyl group, an isobutyl group, a n-pentyl group, a neopentyl group, a tert-pentyl group, a n-hexyl group, a n-octyl group, a n-decyl group, a n-dodecyl group, a n-pentdecyl group and a n-eicosyl group.

These alkyl groups may be substituted with a halogen atom such as a fluorine atom, a chlorine atom, a bromine atom or an iodine atom. Alkyl groups substituted with the halogen atom include, for example, a fluoromethyl group, a trifluoromethyl group, a chloromethyl group, a trichloromethyl group, a fluoroethyl group, a pentafluoroethyl group, a perfluoropropyl group, a perfluorobutyl group, a perfluorohexyl group, a perfluorooctyl group, perchloropropyl group, a per chlorobutyl group and perbromopropyl group. These alkyl groups may be also substituted with an alkoxy group such as a methoxy group or an ethoxy group, an aryloxy group such as a phenoxy group, or an aralkyloxy group such as a benzyloxy group.

The alkyl group as $X^8$ is preferably an alkyl group having 1 to 20 carbon atoms, more preferably a methyl group, an ethyl group, a n-propyl group, an isopropyl group, a tert-butyl group, an isobutyl group and a tert-pentyl group.

The aralkyl group as $X^8$, includes, for example, a benzyl group, a (2-methylphenyl)methyl group, a (3-methylphenyl) methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl) methyl group, a (3,5-dimethylphenyl)methyl group, a (2,3, 4-timethylphenyl)methyl group, a (2,3,5-timethylphenyl) methyl group, a (2,3,6-timethylphenyl)methyl group, a (3,4, 5-timethylphenyl)methyl group, a (2,4,6-timethylphenyl) methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl)methyl group, an (ethylphenyl)methyl group, a (n-propylphenyl) methyl group, an (isopropylphenyl)methyl group, a (n-butylphenyl)methyl group, a (sec-butylphenyl)methyl group, a (tert-butylphenyl)methyl group, a (n-pentylphenyl)methyl group, a (neopentylphenyl)methyl group, a (n-hexylphenyl) methyl group, a (n-octylphenyl)methyl group, a (n-decylphenyl)methyl group, a (tetradecylphenyl) methyl group, a naphthylmethyl group and an anthracenylmethyl group.

These aralkyl groups may be substituted with a halogen atom such as a fluorine atom, a chlorine atom, a bromine atom or an iodine atom, an alkoxy group such as a methoxy group or an ethoxy group, an aryloxy group such as a phenoxy group, or an aralkyloxy group such as a benzyloxy group.

The aralkyl group as $X^8$ is preferably an aralkyl group having 7 to 20 carbon atoms, and more preferably a benzyl group.

As the aryl group as $X^8$, examples thereof include a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, a n-propylphenyl group, an isopropylphenyl group, a n-butylphenyl group, a sec-butylphenyl group, a tert-butylphenyl group, an isobutylphenyl group, a n-pentylphenyl group, a neopentylphenyl group, a n-hexylphenyl group, a n-octylphenyl group, a n-decylphenyl group, a n-dodecylphenyl group, a n-tetradecylphenyl group, a naphthyl group and an anthracenyl group.

These aryl groups may be substituted with a halogen atom such as a fluorine atom, a chlorine atom, a bromine atom or an iodine atom, an alkoxy group such as a methoxy group or an ethoxy group, an aryloxy group such as a phenoxy group, or an aralkyloxy group such as a benzyloxy group.

The aryl group is preferably an aryl group having 6 to 20 carbon atoms, and more preferably a phenyl group.

The hydrocarbonoxy group as $X^8$ includes, for example, alkoxy groups, aryloxy groups and aralkyloxy groups, preferably alkoxy groups having 1 to 20 carbon atoms, aryloxy groups having 6 to 20 carbon atoms and aralkyloxy groups having 7 to 20 carbon atoms. Specific examples thereof include hydrocarbon oxy groups which are mentioned above as those of $L^1$, a (2-methylphenyl)methoxy group, a (3-methylphenyl)methoxy group, a (4-methylphenyl)methoxy group, a (2,3-dimethylphenyl)methoxy group, a (2,4-dimethylphenyl)methoxy group, a (2,5-dimethylphenyl)methoxy group, a (2,6-dimethylphenyl)methoxy group, a (3,4-dimethylphenyl)methoxy group, a (3,5-dimethylphenyl)methoxy group, a (2,3,4-trimethylphenyl)methoxy group, a (2,3,5-trimethylphenyl)methoxy group and benzyloxy group, more preferably a methoxy group, an ethoxy group, an isopropoxy group, a tert-butyl group, an isobutoxy group, phenoxy group, 2,6-di(tert-butyl)phenoxy group and benzyloxy group, further preferably a methoxy group, phenoxy group, 2,6-di(tert-butyl)phenoxy group and benzyloxy group, particularly preferably a methoxy group and phenoxy group.

As $X^8$, a chlorine atom, a methyl group, an ethyl group, a n-propyl group, an isopropyl group, a n-butyl group, a benzyl group, an-allyl group, a methallyl group, a methoxy group, an ethoxy group and a phenoxy group are preferable, and a chlorine atom, a methyl group, a methoxy group and phenoxy group are more preferable.

In the formula [7], "a" represents a numeral satisfying an expression of 0<a≦8, "b" represents a numeral satisfying an expression of 0<b≦8, and "a" and "b" are properly selected depending on the valency of $M^6$.

Among the metal compounds represented by the formula [7] above, specific examples of the compound in which $M^6$ is a titanium atom, include dimethylsilylenebis(cyclopentadienyl)titanium dichloride, dimethylsilylenebis(2-methylcyclopentadienyl)titanium dichloride, dimethylsilylenebis(3-methylcyclopentadienyl)titanium dichloride, dimethylsilylenebis(2-n-butylcyclopentadienyl)titanium dichloride, dimethylsilylenebis(3-n-butylcyclopentadienyl)titanium dichloride, dimethylsilylenebis(2,3-dimethylcyclopentadienyl)titanium dichloride, dimethylsilylenebis(2,4-dimethylcyclopentadienyl)titanium dichloride, dimethylsilylenebis(2,5-dimethylcyclopentadienyl)titanium dichloride, dimethylsilylenebis(3,4-dimethylcyclopentadienyl)titanium dichloride, dimethylsilylenebis(2,3-ethylmethylcyclopentadienyl)titanium dichloride, dimethylsilylenebis(2,4-ethylmethylcyclopentadienyl)titanium dichloride, dimethylsilylenebis(2,5-ethylmethylcyclopentadienyl)titanium dichloride, dimethylsilylenebis(3,5-ethylmethylcyclopentadienyl)titanium dichloride, dimethylsilylenebis(2,3,4-trimethylcyclopentadienyl)titanium dichloride, dimethylsilylenebis(2,3,5-trimethylcyclopentadienyl)titanium dichloride, dimethylsilylenebis(tetramethylcyclopentadienyl)titanium dichloride, dimethylsilylenebis(indenyl)titanium dichloride, dimethylsilylenebis(4,5,6,7-tetrahydroindenyl)titanium dichloride, dimethylsilylene (cyclopentadienyl)(indenyl)titanium dichloride, dimethylsilylene(methylcyclopentadienyl)(indenyl)titanium dichloride, dimethylsilylene(n-butylcyclopentadienyl)(indenyl)titanium dichloride, dimethylsilylene(tetramethylcyclopentadienyl)(indenyl)titanium dichloride, dimethylsilylene (cyclopentadienyl)(fluorenyl)titanium dichloride, dimethylsilylene(methylcyclopentadienyl)(fluorenyl)titanium dichloride, dimethylsilylene(n-butylcyclopentadienyl)(fluorenyl)titanium dichloride, dimethylsilylene(tetramethylcyclopentadienyl)(fluorenyl) titanium dichloride, dimethylsilylene(indenyl)(fluorenyl)titanium dichloride and compounds in which dimethylsilylene is replaced with diethylsilylene, diphenylsilylene or dimethoxysilylene in the above-described compounds.

Further, specific examples of the compound in which $M^6$ is a titanium atom, include bis(cyclopentadienyl)titanium dichloride, bis(methylcyclopentadienyl)titanium dichloride, bis(n-butylcyclopentadienyl)titanium dichloride, bis(dimethylcyclopentadienyl)titanium dichloride, bis(ethylmethylcyclopentadienyl)titanium dichloride, bis(trimethylcyclopentadienyl)titanium dichloride, bis (tetramethylcyclopentadienyl)titanium dichloride, bis (pentamethylcyclopentadienyl)titanium dichloride, bis (indenyl)titanium dichloride, bis(4,5,6,7-tetrahydroindenyl) titanium dichloride, bis(fluorenyl)titanium dichloride, bis(2-phenylindenyl)titanium dichloride, bis[2-(bis-3,5-trifluoromethylphenyl)indenyl]titanium dichloride, bis[2-(4-tert-butylphenyl)indenyl]titanium dichloride, bis[2-(4-trifluoromethylphenyl)indenyl]titanium dichloride, bis[2-(4-methylphenyl)indenyl]titanium dichloride, bis[2-(3,5-dimethylphenyl)indenyl]titanium dichloride, bis[2-(pentafluorophenyl)indenyl]titanium dichloride, cyclopentadienyl(pentamethylcyclopentadienyl)titanium dichloride, cyclopentadienyl(indenyl)titanium dichloride, cyclopentadienyl(fluorenyl)titanium dichloride, indenyl (fluorenyl)titanium dichloride, pentamethylcyclopentadienyl(indenyl)titanium dichloride, pentamethylcyclopentadienyl(fluorenyl)titanium dichloride, cyclopentadienyl(2- phenylindenyl)titanium dichloride, pentamethylcyclopentadienyl(2-phenylindenyl)titanium dichloride, ethylenebis(cyclopentadienyl)titanium dichloride, ethylenebis(2-methylcyclopentadienyl)titanium dichloride, ethylenebis(3-methylcyclopentadienyl)titanium dichloride, ethylenebis(2-n-butylcyclopentadienyl)titanium dichloride, ethylenebis(3-n-butylcyclopentadienyl)titanium dichloride, ethylenebis(2,3-dimethylcyclopentadienyl)titanium dichloride, ethylenebis(2,4-dimethylcyclopentadienyl)titanium dichloride, ethylenebis(2,5-dimethylcyclopentadienyl)titanium dichloride, ethylenebis(3,4-dimethylcyclopentadienyl)titanium dichloride, ethylenebis(2,3-ethylmethylcyclopentadienyl)titanium dichloride, ethylenebis(2,4-ethylmethylcyclopentadienyl)titanium dichloride, ethylenebis(2,5-ethylmethylcyclopentadienyl)titanium dichloride, ethylenebis(3,5-ethylmethylcyclopentadienyl)titanium dichloride, ethylenebis(2,3,4-trimethylcyclopentadienyl)titanium dichloride, ethylenebis(2,3,5-trimethylcyclopentadienyl)titanium dichloride, ethylenebis(tetramethylcyclopentadienyl)titanium dichloride, ethylenebis(indenyl)titanium dichloride, ethylenebis(4,5,6,7-tetrahydroindenyl)titanium dichloride, ethylenebis(2-phenylindenyl)titanium dichloride, ethylenebis(fluorenyl)titanium dichloride, ethylene(cyclopentadienyl)(pentamethylcyclopentadienyl)titanium dichloride, ethylene(cyclopentadienyl)(indenyl)titanium dichloride, ethylene(methylcyclopentadienyl)(indenyl)titanium dichloride, ethylene(n-butylcyclopentadienyl)(indenyl)titanium dichloride, ethylene(tetramethylcyclopentadienyl)(indenyl)titanium dichloride, ethylene(cyclopentadienyl)(fluorenyl)titanium dichloride, ethylene(methylcyclopentadienyl)(fluorenyl)titanium dichloride, ethylene(pentamethylcyclopentadienyl)(fluorenyl)titanium dichloride, ethylene(n-butylcyclopentadienyl)(fluorenyl)titanium dichloride, ethylene(tetramethylpentadienyl)(fluorenyl)titanium dichloride, ethylene(indenyl)(fluorenyl)titanium dichloride, isopropylidenebis(cyclopentadienyl)titanium dichloride, isopropylidenebis(2-methylcyclopentadienyl)titanium dichloride, isopropylidenebis(3-methylcyclopentadienyl)titanium dichloride, isopropylidenebis(2-n-butylcyclopentadienyl)titanium dichloride, isopropylidenebis(3-n-butylcyclopentadienyl)titanium dichloride, isopropylidenebis(2,3-dimethylcyclopentadienyl)titanium dichloride, isopropylidenebis(2,4-dimethylcyclopentadienyl)titanium dichloride, isopropylidenebis(2,5-dimethylcyclopentadienyl)titanium dichloride, isopropylidenebis(3,4-dimethylcyclopentadienyl)titanium dichloride, isopropylidenebis(2,3-ethylmethylcyclopentadienyl)titanium dichloride, isopropylidenebis(2,4-ethylmethylcyclopentadienyl)titanium dichloride, isopropylidenebis(2,5-ethylmethylcyclopentadienyl)titanium dichloride, isopropylidenebis(3,5-ethylmethylcyclopentadienyl)titanium dichloride, isopropylidenebis(2,3,4-trimethylcyclopentadienyl)titanium dichloride, isopropylidenebis(2,3,5-trimethylcyclopentadienyl)titanium dichloride, isopropylidenebis(tetramethylcyclopentadienyl)titanium dichloride, isopropylidenebis(indenyl)titanium dichloride, isopropylidenebis(4,5,6,7-tetrahydroindenyl)titanium dichloride, isopropylidenebis(2-phenylindenyl)titanium dichloride, isopropylidenebis(fluorenyl)titanium dichloride, isopropylidene(cyclopentadienyl)(tetramethylcyclopentadienyl)titanium dichloride, isopropylidene(cyclopentadienyl)(indenyl)titanium dichloride, isopropylidene(methylcyclopentadienyl)(indenyl)titanium dichloride, isopropylidene(n-butylcyclopentadienyl)(indenyl)titanium dichloride, isopropylidene(tetramethylcyclopentadienyl)(indenyl)titanium dichloride, isopropylidene (cyclopentadienyl)(fluorenyl)titanium dichloride, isopropylidene (methylcyclopentadienyl)(fluorenyl)titanium dichloride, isopropylidene(n-butylcyclopentadienyl)(fluorenyl)titanium dichloride, isopropylidene(tetramethylcyclopentadienyl)(fluorenyl)titanium dichloride, isopropylidene (indenyl)(fluorenyl)titanium dichloride, cyclopentadienyl(dimethylamido)titanium dichloride, cyclopentadienyl(phenoxy)titanium dichloride, cyclopentadienyl(2,6-dimethylphenyl)titanium dichloride, cyclopentadienyl(2,6-diisopropylphenyl)titanium dichloride, cyclopentadienyl(2,6-di-tert-butylphenyl)titanium dichloride, pentamethylcyclopentadienyl(2,6-dimethylphenyl)titanium dichloride, pentamethylcyclopentadienyl(2,6-diisopropylphenyl)titanium dichloride, pentamethylcyclopentadienyl(2,6-di-tert-butylphenyl)titanium dichloride, indenyl(2,6-diisopropylphenyl)titanium dichloride, fluorenyl(2,6-diisopropylphenyl)titanium dichloride, (tert-butylamido)tetramethylcyclopentadienyl-1,2-ethanediyltitanium dichloride, (methylamido)tetramethylcyclopentadienyl-1,2-ethanediyltitanium dichloride, (ethylamido)tetramethylcyclopentadienyl-1,2-ethanediyltitanium dichloride, (tert-butylamido)tetramethylcyclopentadienyl dimethylsilanetitanium dichloride,(benzylamido)tetramethylcyclopentadienyl dimethylsilanetitanium dichloride, (phenylphosphido)tetramethylcyclopentadienyl dimethylsilanetitanium dichloride, (tert-butylamido)indenyl-1,2-ethanediyltitanium dichloride, (tert-butylamido)tetrahydroindenyl-1,2-ethanediyltitanium dichloride, (tert-butylamido)fluorenyl-1,2-ethanediyltitanium dichloride, (tert-butylamido)indenyldimethylsilanetitanium dichloride, (tert-butylamido)tetrahydroindenyldimethylsilane titanium dichloride, (tert-butylamido)fluorenyldimethylsilanetitanium dichloride, (dimethylaminomethyl)tetramethylcyclopentadienyl titanium(III)dichloride, (dimethylaminoethyl)tetramethylcyclopentadienyl titanium(III)dichloride, (dimethylaminopropyl)tetramethylcyclopentadienyl-titanium (III)dichloride, (N-pyrrolidinylethyl)tetramethylcyclopentadienyl-titanium dichloride, (B-dimethylaminoborabenzene)cyclopentadienylzirconium dichloride, cyclopentadienyl(9-mesitylboraanthracenyl)zirconium dichloride, 2,2'-thiobis(4-methyl-6-tert-butylphenoxy)titanium dichloride, 2,2'-thiobis[4-methyl-6-(1-methylethyl)phenoxy]titanium dichloride, 2,2'-thiobis[4,6-dimethylphenoxy]titanium dichloride, 2,2'-methylenebis(4-methyl-6-tert-butylphenoxy) titanium dichloride, 2,2'-ethylenebis(4-methyl-6-tert-butylphenoxy) titanium dichloride, 2,2'-sulfinylbis(4-methyl-6-tert-butylphenoxy) titanium dichloride, 2,2'-(4,4',6,6'-tetra-tert-butyl-1,1'-biphenoxy) titanium dichloride, (di-tert-butyl-1,3-propanediamido)titanium dichloride, (dicyclohexyl-1,3-propanediamido)titanium dichloride, [bis(trimethylsilyl)-1,3-propanediamido]titanium dichloride, [bis(tert-butyldimethylsilyl)-1,3-propanediamido]titanium dichloride, [bis(2,6-dimethylphenyl)-1,3-propanediamido]titanium dichloride, [bis(2,6-diisopropylphenyl)-1,3-propanediamido]titanium dichloride, [bis(2,6-di-tert-butylphenyl)-1,3-propanediamido]titanium dichloride, [bis(triisopropylsilyl)naphthalenediamido]titanium dichloride, [bis(trimethylsilyl)naphthalenediamido]titanium dichloride, [bis(tert-butyldimethylsilyl)naphthalenediamido]titanium dichloride, [bis(tert-butyldimethylsilyl)naphthalenediamido]titanium dibromide, cyclopentadienyltitanium trichloride, pentamethylcyclopentadienyltitanium trichloride, [hydrotris(3,5-dimethylpyrazolyl)borate]titanium trichloride, [hydrotris(3,5-diethylpyrazolyl)borate]titanium trichloride, [hydrotris(3,5-di-tert-butylpyrazolyl)borate]titanium trichloride, [tris(3,5-dimethylpyrazolyl)methyl]titanium trichloride, [tris(3,5- diethylpyrazolyl)methyl]titanium trichloride and [tris(3,5-di-tert-butylpyrazolyl)methyl]titanium trichloride.

Furthermore, specific examples of the compound in which $M^6$ is a titanium atom, include compounds in which dichloride of these compounds is replaced with difluoride, dibromide, diiodide, dimethyl, diethyl, diisopropyl, diphenyl, dibenzyl, dimethoxide, diethoxide, di-n-propoxide, diisopropoxide, di-n-butoxide, diisobutoxide, di-tert-butoxide, diphenoxide or di(2,6-di-tert-butylphenoxide, and compounds in which trichloride of these compounds is replaced with trifluoride, tribromide, triiodide, trimethyl, triethyl, triisopropyl, triiphenyl, tribenzyl, trimethoxide, triethoxide, tri-n-propoxide, triisopropoxide, tri-n-butoxide, triisobutoxide, tri-tert-butoxide, triphenoxide or tri(2,6-di-tert-butylphenoxide.

Moreover, among the metal compounds represented by the formula [7], specific examples of compounds in which $M^6$ in the formula [7] is zirconium or hafnium, include those in which a titanium atom is repleced with a zirconium atom or a hafnium atom in titanium compounds above-described.

Furthermore, among the metal compounds represented by the formula [7], specific examples of compounds in which a metal atom is nickel atom include 2,2'-methylenebis[(4R)-4-phenyl-5,5'-dimethyloxazoline]nickel dibromide, $2,2^1$-methylenebis[(4R)-4-phenyl-5,5'-diethyloxazoline]nickel dibromide, 2,2'-methylenebis[(4R)-4-phenyl-5,5'-di-n-propyloxazoline]nickel dibromide, 2,2'-methylenebis[(4R)-4-phenyl-5,5'-diisopropyloxazoline]nickel dibromide, 2,2'-methylenebis[(4R)-4-phenyl-5,5'-dicyclohexyloxazoline]nickel dibromide, 2,2'-methylenebis[(4R)-4-phenyl-5,5'-dimethoxyoxazoline]nickel dibromide, 2,2'-methylenebis[(4R)-4-phenyl-5,5'-diethoxyoxazoline]nickel dibromide, 2,2'-methylenebis[(4R)-4-phenyl-5,5'-diphenyloxazoline]nickel dibromide, methylenebis[(4R)-4-methyl-5,5'-di-(2-methylphenyl)oxazoline]nickel dibromide, methylenebis[(4R)-4-methyl-5,5'-di-(3-methylphenyl)oxazoline]nickel dibromide, methylenebis[(4R)-4-methyl-5,5'-di-(4-methylphenyl)oxazoline]nickel dibromide, methylenebis[(4R)-4-methyl-5,5'-di-(2-methoxyphenyl)oxazoline]nickel dibromide, methylenebis[(4R)-4-methyl-5,5'-di-(3-methoxyphenyl)oxazoline]nickel dibromide, methylenebis[(4R)-4-methyl-5,5'-di-(4-methoxyphenyl)oxazoline]nickel dibromide, methylenebis[spiro{(4R)-4-methyloxazoline-5,1'-cyclobutane}]nickel dibromide, methylenebis[spiro{(4R)-4-methyloxazoline-5,1'-cyclopentane}]nickel dibromide, methylenebis[spiro{(4R)-4-methyloxazoline-5,1'-cyclohexane}]nickel dibromide, methylenebis[spiro{(4R)-4-methyloxazoline-5,1'-cycloheptane}]nickel dibromide, 2,2'-methylenebis[(4R)-4-isopropyl-5,5-dimethyloxazoline]nickel dibromide, 2,2'-methylenebis[(4R)-4-isopropyl-5,5-diethyloxazoline]nickel dibromide, 2,2'-methylenebis[(4R)-4-isopropyl-5,5-di-n-propyloxazoline]nickel dibromide, methylenebis[(4R)-4-isopropyl-5,5-diisopropyloxazoline]nickel dibromide, 2,2'-methylenebis[(4R)-4-isopropyl-5,5-dicyclohexyloxazoline]nickel dibromide, 2,2'-methylenebis[(4R)-4-isopropyl-5,5-diphenyloxazoline]nickel dibromide, 2,2'-methylenebis[(4R)-4-isopropyl-5,5-di-(2-methylphenyl)oxazoline]nickel dibromide, 2,2'-methylenebis[(4R)-4-isopropyl-5,-di-(3-methylphenyl)oxazoline]nickel dibromide, 2,2'-methylenebis[(4R)-4-isopropyl-5,5-di-(4-methylphenyl)oxazoline]nickel dibromide, 2,2'-methylenebis[(4R)-4-isopropyl-5,5-di-(2-methoxyphenyl)oxazoline]nickel dibromide, 2,2'-methylenebis[(4R)-4-isopropyl-5,5-di-(3-methoxyphenyl)oxazoline]nickel dibromide, 2,2'-methylenebis[(4R)-4-isopropyl-5,5-di-(4-methoxyphenyl)oxazoline]nickel dibromide, 2,2'-methylenebis[spiro{(4R)-4-isopropyloxazoline-5,1'-cyclobutane}] nickel dibromide, 2,2'-methylenebis[spiro{(4R)-4-isopropyloxazoline-5,1'-cyclopentane}]nickel dibromide, 2,2'-methylenebis[spiro{(4R)-4-isopropyloxazoline-5,1'-cyclohexane}]nickel dibromide, 2,2'-methylenebis[spiro{(4R)-4-isopropyloxazoline-5,1'-cycloheptane}]nickel dibromide, 2,2'-methylenebis[(4R)-4-isobutyl-5,5-dimethyloxazoline]nickel dibromide, 2,2'-methylenebis[(4R)-4-isobutyl-5,5-diethyloxazoline]nickel dibromide, 2,2'-methylenebis[(4R)-4-isobutyl-5,5-di-n-propyloxazoline]nickel dibromide, 2,2'-methylenebis[(4R)-4-isobutyl-5,5-diisopropyloxazoline]nickel dibromide, 2,2'-methylenebis[(4R)-4-isobutyl-5,5-dicyclohexyloxazoline]nickel dibromide, 2,2'-methylenebis[(4R)-4-isobutyl-5,5-diphenyloxazoline]nickel dibromide, 2,2'-methylenebis[(4R)-4-isobutyl-5,5-di-(2-methylphenyl)oxazoline]nickel dibromide, 2,2'-methylenebis[(4R)-4-isobutyl-5,5-di-(3-methylphenyl)oxazoline]nickel dibromide, 2,2'-methylenebis[(4R)-4-isobutyl-5,5-di-(4-methylphenyl)oxazoline]nickel dibromide, 2,2'-methylenebis[(4R)-4-isobutyl-5,5-di-(2-methoxyphenyl)oxazoline]nickel dibromide, 2,2'-methylenebis[(4R)-4-isobutyl-5,5-di-(3-methoxyphenyl)oxazoline]nickel dibromide, 2,2'-methylenebis[(4R)-4-isobutyl-5,5-di-(4-methoxyphenyl)oxazoline]nickel dibromide, 2,2'-methylenebis[spiro{(4R)-4-isobutyloxazoline-5,1'-cyclobutane}]nickel dibromide, 2,2'-methylenebis[spiro{(4R)-4-isobutyloxazoline-5,1'-cyclopentane}]nickel dibromide, 2,2'-methylenebis[spiro{(4R)-4-isobutyloxazoline-5,1'-cyclohexane}]nickel dibromide, 2,2'-methylenebis[spiro{(4R)-4-isobutyloxazoline-5,1'-cycloheptane}]nickel dibromide, 2,2'-methylenebis[(4R)-4-tert-butyl-5,5-dimethyloxazoline]nickel dibromide, 2,2'-methylenebis[(4R)-4-tert-butyl-5,5-diethyloxazoline]nickel dibromide, 2,2'-methylenebis[(4R)-4-tert-butyl-5,5-di-n-propyloxazoline]nickel dibromide, 2,2'-methylenebis[(4R)-4-tert-butyl-5,5-diisopropyloxazoline]nickel dibromide, 2,2'-methylenebis[(4R)-4-tert-butyl-5,5-diphenyloxazoline]nickel dibromide, 2,2'-methylenebis[(4R)-4-tert-butyl-5,5-dicyclohexyloxazoline]nickel dibromide, 2,2'-methylenebis[(4R)-4-tert-butyl-5,5-di-(2-methylphenyl)oxazoline]nickel dibromide, 2,2'-methylenebis[(4R)-4-tert-butyl-5,5-di-(3-methylphenyl)oxazoline]nickel dibromide, 2,2'-methylenebis[(4R)-4-tert-butyl-5,5-di-(4-methylphenyl)oxazoline]nickel dibromide, 2,2'-methylenebis[(4R)-4-tert-butyl-5,5-di-(2-methoxyphenyl)oxazoline]nickel dibromide, 2,2'-methylenebis[(4R)-4-tert-butyl-5,5-di-(3-methoxyphenyl)oxazoline]nickel dibromide, 2,2'-methylenebis[(4R)-4-tert-butyl-5,5-di-(4-methoxyphenyl)oxazoline]nickel dibromide, 2,2'-methylenebis[spiro{(4R)-4-tert-butyloxazoline-5,1'-cyclobutane}]nickel dibromide, 2,2'-methylenebis[spiro{(4R)-4-tert-butyloxazoline-5,1'-cyclopentane}]nickel dibromide, 2,2'-methylenebis[spiro{(4R)-4-tert-butyloxazoline-5,1'-cyclohexane}]nickel dibromide, 2,2'-methylenebis[spiro{(4R)-4-tert-butyloxazoline-5,1'-cycloheptane}]nickel dibromide, 2,2'-methylenebis[(4R)-4-phenyl-5,5-dimethyloxazoline]nickel dibromide, 2,2'-methylenebis[(4R)-4-phenyl-5,5-diethyloxazoline]nickel dibromide, 2,2'-methylenebis[(4R)-4-phenyl-5,5-di-n-propyloxazoline)nickel dibromide, 2,2'-methylenebis[(4R)-4-phenyl-5,5-diisopropyloxazoline]nickel dibromide, 2,2'-methylenebis[(4R)-4-phenyl-5,5-dicyclohexyloxazoline]nickel dibromide, 2,2'-methylenebis[(4R)-4-phenyl-5,5-diphenyl]oxazoline]nickel dibromide, 2,2'-methylenebis[(4R)-4-phenyl-5,5-di-(2-methylphenyl)oxazoline]nickel dibromide, 2,2'-methylenebis[(4R)-4-phenyl-5,5-di-(3-methylphenyl)oxazoline]nickel dibromide, 2,2'-methylenebis[(4R)-4-phenyl-5,5-di-(4-methylphenyl)oxazoline]nickel dibromide, 2,2'-methylenebis[(4R)-4-phenyl-5,5-di-(2- methoxyphenyl)oxazoline]nickel dibromide, 2,2'-methylenebis[(4R)-4-phenyl-5,5-di-(3-methoxyphenyl)oxazoline] nickel dibromide, 2,2'-methylenebis[(4R)-4-phenyl-5,5-di-(4-methoxyphenyl)oxazoline]nickel dibromide, methylenebis[spiro{(4R)-4-phenyloxazoline-5,1'-cyclobutane}]nickel dibromide, 2,2'-methylenebis[spiro{(4R)-4-phenyloxazoline-5,1'-cyclopentane}]nickel dibromide, 2,2'-methylenebis[spiro{(4R)-4-phenyloxazoline-5,1'-cyclohexane}]nickel dibromide, 2,2'-methylenebis[spiro{(4R)-4-phenyloxazoline-5,1'-cycloheptane}]nickel dibromide, 2,2'-methylenebis[(4R)-4-benzyl-5,5-dimethyloxazoline]nickel dibromide, 2,2'-methylenebis[(4R)-4-benzyl-5,5-diethyloxazoline]nickel dibromide, 2,2'-methylenebis[(4R)-4-benzyl-5,5-di-n-propyloxazoline]nickel dibromide, 2,2'-methylenebis[(4R)-4-benzyl-5,5-diisopropyloxazoline]nickel dibromide, 2,2'-methylenebis[(4R)-4-benzyl-5,5-dicyclohexyloxazoline]nickel dibromide, 2,2'-methylenebis[(4R)-4-benzyl-5,5-diphenyl]oxazoline]nickel dibromide, 2,2'-methylenebis[(4R)-4-benzyl-5,5-di-(2-methylphenyl)oxazoline]nickel dibromide, 2,2'-methylenebis[(4R)-4-benzyl-5,5-di-(3-methylphenyl)oxazoline]nickel dibromide, 2,2'-methylenebis[(4R)-4-benzyl-5,5-di-(4-methylphenyl)oxazoline]nickel dibromide, 2,2'-methylenebis[(4R)-4-benzyl-5,5-di-(2-methoxyphenyl)oxazoline]nickel dibromide, 2,2'-methylenebis[(4R)-4-benzyl-5,5-di-(3-methoxyphenyl)oxazoline]nickel dibromide, 2,2'-methylenebis[(4R)-4-benzyl-5,5-di-(4-methoxyphenyl)oxazoline] nickel dibromide, 2,2'-methylenebis[spiro{(4R)-4-benzyloxazoline-5,1'-cyclobutane}]nickel dibromide, 2,2'-methylenebis[spiro{(4R)-4-benzyloxazoline-5,1'-cyclopentane}]nickel dibromide, 2,2'-methylenebis[spiro{(4R)-4-benzyloxazoline-5,1'-cyclohexane}]nickel dibromide, 2,2'-methylenebis[spiro{(4R)-4-benzyloxazoline-5,1'-cycloheptane}]nickel dibromide, antipodes and diastreomers of compounds described above. Further, specific examples of the nickel compounds include [hydrotris(3,5-dimethylpyrazolyl)borate]nickel bromide, [hydrotris(3,5-diethylpyrazolyl)borate]nickel bromide and [hydrotris(3,5-di-tert-butylpyrazolyl)borate]nickel bromide.

Furthermore, compounds in which dibromide of these compounds listed above is replaced with difluoride, dichloride, diiodide, dimethyl, diethyl, diisopropyl, diphenyl, dibenzyl, dimethoxide diethoxide, di-n-propoxide, diisopropoxide, di-n-butoxide, diisobutoxide, di-tert-butoxide, diphenoxide or di(2,6-di-tert-butylphenoxide) are also listed.

Moreover, specific examples of nickel compounds include those represented by the chemical formula (101 described below:

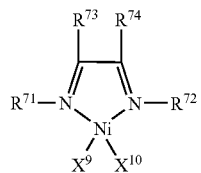

[10]

(wherein each of $R^{71}$ and $R^{72}$ is a 2,6-diisopropylphenyl group, and $X^9$, $X^{10}$, $R^{73}$ and $R^{74}$ are any one of the combination of the substituents represented in Table 1 described below.)

TABLE 1

| | | |
|---|---|---|
| $R^{73} = R^{74} = H$ | $R^{73} = R^{74}$ = methyl | Acenaphthyl by $R^{73}$ & $R^{74}$ |
| $X^9 = X^{10} = F$ | $X^9 = X^{10} = F$ | $X^9 = X^{10} = F$ |
| $R^{73} = R^{74} = H$ | $R^{73} = R^{74}$ = methyl | Acenaphthyl by $R^{73}$ & $R^{74}$ |
| $X^9 = X^{10} = Cl$ | $X^9 = X^{10} = Cl$ | $X^9 = X^{10} = Cl$ |
| $R^{73} = R^{74} = H$ | $R^{73} = R^{74}$ = methyl | Acenaphthyl by $R^{73}$ & $R^{74}$ |
| $X^9 = X^{10} = I$ | $X^9 = X^{10} = I$ | $X^9 = X^{10} = I$ |
| $R^{73} = R^{74} = H$ | $R^{73} = R^{74}$ = methyl | Acenaphthyl by $R^{73}$ & $R^{74}$ |
| $X^9 = X^{10}$ = Methyl | $X^9 = X^{10}$ = methyl | $X^9 = X^{10}$ = methyl |
| $R^{73} = R^{74} = H$ | $R^{73} = R^{74}$ = methyl | Acenaphthyl by $R^{73}$ & $R^{74}$ |
| $X^9 = X^{10}$ = Ethyl | $X^9 = X^{10}$ = ethyl | $X^9 = X^{10}$ = ethyl |
| $R^{73} = R^{74} = H$ | $R^{73} = R^{74}$ = methyl | Acenaphthyl by $R^{73}$ & $R^{74}$ |
| $X^9 = X^{10}$ = n-propyl | $X^9 = X^{10}$ = n-propyl | $X^9 = X^{10}$ = n-propyl |
| $R^{73} = R^{74} = H$ | $R^{73} = R^{74}$ = methyl | Acenaphthyl by $R^{73}$ & $R^{74}$ |
| $X^9 = X^{10}$ = isopropyl | $X^9 = X^{10}$ = isopropyl | $X^9 = X^{10}$ = isopropyl |
| $R^{73} = R^{74} = H$ | $R^{73} = R^{74}$ = methyl | Acenaphthyl by $R^{73}$ & $R^{74}$ |
| $X^9 = X^{10}$ = n-butyl | $X^9 = X^{10}$ = n-butyl | $X^9 = X^{10}$ = n-butyl |
| $R^{73} = R^{74} = H$ | $R^{73} = R^{74}$ = methyl | Acenaphthyl by $R^{73}$ & $R^{74}$ |
| $X^9 = X^{10}$ = phenyl | $X^9 = X^{10}$ = phenyl | $X^9 = X^{10}$ = phenyl |
| $R^{73} = R^{74} = H$ | $R^{73} = R^{74}$ = methyl | Acenaphthyl by $R^{73}$ & $R^{74}$ |
| $X^9 = X^{10}$ = benzyl | $X^9 = X^{10}$ = benzyl | $X^9 = X^{10}$ = benzyl |

Further, compounds in which a nickel atom is replaced with a palladium atom, a cobalt atom, a rhodium atom or a ruthenium atom can be similarly exemplified in the above-mentioned nickel compounds.

Among the metal compounds represented by the formula [7], specific examples of a compound in which a transition metal atom is an iron atom include 2,6-bis-[1-(2,6-dimethylphenylimino)ethyl]pyridineiron dichloride, 2,6-bis-[1-(2,6-diisopropylphenylimino)ethyl]pyridineiron dichloride, 2,6-bis-[1-(2-tert-butylphenylimino)ethyl]pyridineiron dichloride, [hydrotris(3,5-dimethylpyrazolyl)borate]iron chloride, [hydrotris(3,5-diethylpyrazolyl) borate)iron chloride, [hydrotris(3,5-di-tert-butylpyrazolyl)borate]iron chloride, and compounds in which dichloride is replaced with dibromide, difluoride, diiodide, dimethyl, diethyl, diisopropyl, diphenyl, dibenzyl, dimethoxide, diethoxide, di-n-propoxide, diisopropoxide, di-n-butoxide, diisobutoxide, di-tert-butoxide, diphenoxide or di(2,6-di-tert-butylphenoxide) in the above-mentined iron compounds.

Further, compounds in which an iron atom is replaced with a cobalt atom or a nickel atom in the above-mentioned iron compounds can be similarly exemplified.

Specific examples of a µ-oxo type compound represented by the formula [7] include µ-oxobis[isopropylidene (cyclopentadienyl)(2-phenoxy)titanium chloride], µ-oxobis[isopropylidene(cyclopentadienyl)(2-phenoxy)titanium methoxide), µ-oxobis[isopropylidene(cyclopentadienyl)(3-tert-butyl-5-methyl-2-phenoxy)titanium chloride], µ-oxobis [isopropylidene(cyclopentadienyl)(3-tert-butyl-5-methyl-2-phenoxy)titanium methoxide], µ-oxobis[isopropylidene (methylcyclopentadienyl)(2-phenoxy)titanium chloride], µ-oxobis[isopropylidene(methylcyclopentadienyl)(2-phenoxy)titanium methoxide], µ-oxobis[isopropylidene(methylcyclopentadienyl)(3-tert-butyl-5-methyl-2-phenoxy)titanium chloride], µ-oxobis[isopropylidene (methylcyclopentadienyl)(3-tert-butyl-5-methyl-2-phenoxy)titanium methoxide], µ-oxobis[isopropylidene (tetramethylcyclopentadienyl)(2-phenoxy)titanium chloride], µ-oxobis[isopropylidene(tetramethylcyclopentadienyl)(2-phenoxy)titanium methoxide], µ-oxobis[isopropylidene(tetramethylcyclopentadienyl)(3-tert-butyl-5-methyl-2-phenoxy)titanium chloride], µ-oxobis[isopropylidene (tetramethylcyclopentadienyl)(3-tert-butyl-5-methyl-2-phenoxy)titanium methoxide], -oxobis[dimethylsilylene (cyclopentadienyl)(2-phenoxy)titanium chloride], µ-oxobis [dimethylsilylene(cyclopentadienyl)(2-phenoxy)titanium methoxide], μ-oxobis[dimethylsilylene(cyclopentadienyl)(3-tert-butyl-5-methyl-2-phenoxy)titanium chloride], μ-oxobis[dimethylsilylene(cyclopentadienyl)(3-tert-butyl-5-methyl-2-phenoxy)titanium methoxide], μ-oxobis[dimethylsilylene(methylcyclopentadienyl)(2-phenoxy)titanium chloride], μ-oxobis[dimethylsilylene(methylcyclopentadienyl)(2-phenoxy)titanium methoxide], μ-oxobis[dimethylsilylene(methylcyclopentadienyl)(3-tert-butyl-5-methyl-2-phenoxy)titanium chloride], μ-oxobis[dimethylsilylene(methylcyclopentadienyl)(3-tert-butyl-5-methyl-2-phenoxy)titanium methoxide], μ-oxobis[dimethylsilylene(tetramethylcyclopentadienyl)(2-phenoxy)titanium chloride], μ-oxobis[dimethylsilylene(tetramethylcyclopentadienyl)(2-phenoxy)titanium methoxide], μ-oxobis[dimethylsilylene(tetramethylcyclopentadienyl)(3-tert-butyl-5-methyl-2-phenoxy)titanium chloride], μ-oxobis[dimethylsilylene(tetramethylcyclopentadienyl)(3-tert-butyl-5-methyl-2-phenoxy)titanium methoxide], di-μ-oxobis[isopropylidene(cyclopentadienyl)(2-phenoxy)titanium], di-μ-oxobis(isopropylidene(cyclopentadienyl)(3-tert-butyl-5-methyl-2-phenoxy)titanium], di-μ-oxobis(isopropylidene(methylcyclopentadienyl)(2-phenoxy)titanium], μ-oxobis[isopropylidene(methylcyclopentadienyl)(3-tert-butyl-5-methyl-2-phenoxy)titanium], di-μ-oxobis[isopropylidene(tetramethylcyclopentadienyl)(2-phenoxy)titanium], di-μ-oxobis[isopropylidene(tetramethylcyclopentadienyl)(3-tert-butyl-5-methyl-2-phenoxy)titanium], di-μ-oxobis[dimethylsilylene(cyclopentadienyl)(2-phenoxy)titanium], di-μ-oxobis[dimethylsilylene(cyclopentadienyl)(3-tert-butyl-5-methyl-2-phenoxy)titanium], di-μ-oxobis[dimethylsilylene(methylcyclopentadienyl)(2-phenoxy)titanium], di-μ-oxobis[dimethylsilylene(methylcyclopentadienyl)(3-tert-butyl-5-methyl-2-phenoxy)titanium], di-μ-oxobis[dimethylsilylene(tetramethylcyclopentadienyl)(2-phenoxy) titanium] and di-μ-oxobis[dimethylsilylene(tetramethylcyclopentadienyl)(3-tert-butyl-5-methyl-2-phenoxy)titanium].

Specific examples of nickel compounds other than the nickel compounds represented by the formula [7] as the metal compound (B) include nickel chloride, nickel bromide, nickel iodide, nickel sulfate, nickel nitrate, nickel perchlorate, nickel acetate, nickel trifluoroacetate, nickel cyanide, nickel oxalate, nickel acetylacetonate, bis(allyl) nickel, bis(1,5-cyclooctadiene)nickel, dichloro(1,5-cyclooctadiene) nickel, dichlorobis(acetonitrile)nickel, dichlorobis(benzonitrile)nickel, carbonyl tris(triphenylphosphine) nickel, dichlorobis(triethylphosphine)nickel, di-acetobis(triphenylphosphine)nickel, tetrakis(triphenylphosphine) nickel, dichloro[1,2-bis(diphenylphosphino)ethane]nickel, bis[1,2-bis(diphenylphosphino)ethane]nickel, dichloro[1,3-bis(diphenylphosphino)propane]nickel, bis[1,3-bis(diphenylphosphino)propane]nickel, tetraamine nickel nitrate, tetrakis(acetonitrile)nickel tetrafluoroborate and nickel phthalocyanine.

And, specific examples of a compound in which a transition metal atom is a vanadium atom include vanadium acetylacetonate, vanadium tetrachloride and vanadium oxy trichloride.

Further, specific examples of a compoundin which a transition metal atom is a samarium atom include bis(pentamethylcyclopentadienyl)samarium methyltetrahydrofuran and the like.

Furthermore, specific examples of a compound in which a transition metal atom is an ytterbium atom include bis(pentamethylcyclopentadienyl)ytterbium methyltetrahydrofuran and the like.

These compounds may be used alone or in combination of two or more. Among the above-mentioned compounds (B), the compounds represented by the formula [7] are preferable. Among them, compounds of the metal of Group 3 to Group 11 of the periodic table of the elements are preferred and particularly, metal compounds in which at least one of $L^2$'s in the formula [7], has a cyclopentadienyl type anion, are preferred.

The catalyst according to claim 11, wherein the monocyclopentadienyl metallic compound is any one of those represented by the chemical formulae [4] to [6] below:

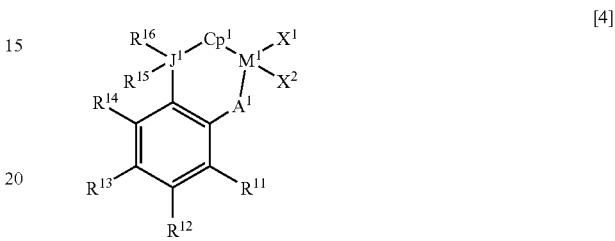

[4]

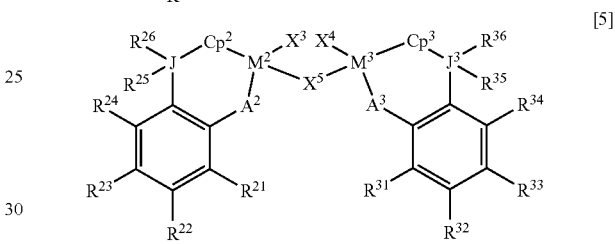

[5]

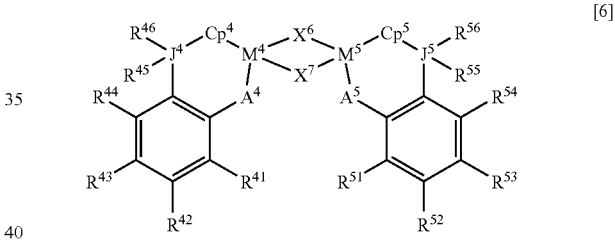

[6]

wherein respective $M^1$ to $M^5$ represent independently an atom of Group 4 of the periodic table of the elements; respective A1 to A5 represent independently an atom of Group 16 of the periodic table of the elements; respective J1 to J5 represent an atom of Group 16 of the periodic table of the elements; respective Cp1 to Cp5 represent a group having a cyclopentadienyl anion skeleton; respective $X^1$ to $X^5$, $R^{11}$ to $R^{16}$, $R^{21}$ to $R^{26}$, $R^{31}$ to $R^{36}$, $R^{41}$ to $R^{46}$ and $R^{51}$ to $R^{56}$ represent independently a hydrogen atom, a halogen atom, a hydrocarbon group, substituted silyl group, a hydrocarbon oxt group, di-substituted amino group, a hydrocarbon thio group or a hydrocarbon seleno group, they may link to form a single ring or a plurarity of rings which may be aromatic ring(s) or non-aromatic ring(s); and respective $X^5$ to $X^7$ represent an atom of Group 16 of the periodic table of the elements.

In the formulae [4] to [6], the metal represented by $M^1$ to $M^5$ represents a metal atom of Group 4 of the Periodic Table (IUPAC 1985), and for example, a titanium atom, a zirconium ato and a hafnium atom are exemplified. A titanium atom and a zirconium atom are preferred.

A group having a cyclopentadienyl type anion skeleton as $Cp^1$ to $Cp^5$ includes an $η^5$-(substituted)cyclopentadienyl group, an $η^5$-(substituted)indenyl group, an $η^5$-(substituted) fluorenyl group and the like. Specific examples thereof include an $\eta^5$-cyclopentadienyl group, an $\eta^5$-methylcyclopentadienyl group, an $\eta^5$-dimethylcyclopentadienyl group, an $\eta^5$-trimethylcyclopentadienyl group, an $\eta^5$-tetramethylcyclopentadienyl group, an $\eta^5$-ethylcyclopentadienyl group, an $\eta^5$-n-propylcyclopentadienyl group, an $\eta^5$-isopropylcyclopentadienyl group, an $\eta^5$-n-butylcyclopentadienyl group, an $\eta^5$-sec-butylcyclopentadienyl group, an $\eta^5$-tert-butylcyclopentadienyl group, an $\eta^5$-phenylcyclopentadienyl group, an $\eta^5$-trimethysilylcyclopentadienyl group, an $\eta^5$-tert-butyldimethylsilylcyclopentadienyl group, an $\eta^5$-indenyl group, an $\eta^5$-methylindenyl group, an $\eta^5$-dimethylindenyl group, an $\eta^5$-n-propylindenyl group, an $\eta^5$-isopropylindenyl group, an $\eta^5$-n-butylindenyl group, an $\eta^5$-tert-butylindenyl group, an $\eta^5$-phenylindenyl group, an $\eta^5$-methylphenylindenyl group, an $\eta^5$-naphthylindenyl group, an $\eta^5$-trimethylsilylindenyl group, an $\eta^5$-tetrahydroindenyl group, an $\eta^5$-fluorenyl group, an $\eta^5$-methylfluorenyl group, an $\eta^5$-dimethylfluorenyl group, an $\eta^5$-tert-butylfluorenyl group, an $\eta^5$-di-tert-butylfluorenyl group, an $\eta^5$-phenylfluorenyl group, an $\eta 5$-diphenylfluorenyl group, an $\eta^5$-trimethysilylfluorenyl group and an $\eta^5$-bistrimethysilylfluorenyl group, preferably an $\eta 5$-cyclopentadienyl group, an $\eta^5$-methylcyclopentadienyl group, an $\eta^5$-n-butylcyclopentadienyl group, an $\eta^5$-tert-butylcyclopentadienyl group, an $\eta^5$-tetramethlcyclopentadienyl group, an $\eta^5$-indenyl group, an $\eta^5$-tetrahydroindenyl group and an $\eta^5$-fluorenyl group.

In $X^1$ to $X^4$, $R^{11}$ to $R^{16}$, $R^{21}$ to $R^{26}$, $R^{31}$ to $R^{36}$, $R^{41}$ to $R^{46}$ and $R^{51}$ to $R^{56}$ of the formula [4] to [6], as a halogen atom, a fluorine atom, a chlorine atom, a bromine atom and an iodine atom are exemplified, a chlorine atom, a bromine atom are preferable, and a chlorine atom is more preferable.

In $X^1$ to $X^4$, $R^{11}$ to $R^{16}$, $R^{21}$ to $R^{26}$, $R^{31}$ to $R^{36}$, $R^{41}$ to $R^{46}$ and $R^{51}$ to $R^{56}$ of the formula [4] to [6], as a hydrocarbon group, an alkyl group, an aralkyl group and aryl group are exemplified.

As the alkyl group, a methyl group, an ethyl group, a n-propyl group, an isopropyl group, a n-butyl group, a sec-butyl group, a tert-butyl group, an isobutyl group, a n-pentyl group, a neopentyl group, a tert-pentyl group, a n-hexyl group, a n-octyl group, a n-decyl group, a n-dodecyl group, n-pentadecyl group and a n-eicosyl group are exemplified.

These alkyl groups may be substituted with a halogen atom such as a fluorine atom, a chlorine atom, a bromine atom or an iodine atom.

Alkyl groups substituted with the halogen atom include, for example, a fluoromethyl group, a trifluoromethyl group, a chloromethyl group, a trichloromethyl group, a fluoroethyl group, a pentafluoroethyl group, a perfluoropropyl group, a perfluorobutyl group, a perfluorohexyl group, a perfluorooctyl group, perchloropropyl group, a per chlorobutyl group and perbromopropyl group.

The alkyl group is preferably an alkyl group having 1 to 20 carbon atoms, more preferably a methyl group, an ethyl group, an isopropyl group, a tert-butyl group, an isobutyl group and a tert-pentyl group.

The aralkyl group includes, for example, a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (3,5-dimethylphenyl)methyl group, a (2,3,4-timethylphenyl)methyl group, a (2,3,5-timethylphenyl)methyl group, a (2,3,6-timethylphenyl)methyl group, a (3,4,5-timethylphenyl)methyl group, a (2,4,6-timethylphenyl)methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl)methyl group, an (ethylphenyl)methyl group, a (n-propylphenyl) methyl group, an (isopropylphenyl)methyl group, a (n-butylphenyl)methyl group, a (sec-butylphenyl)methyl group, a (tert-butylphenyl)methyl group, a (n-pentylphenyl)methyl group, a (neopentylphenyl)methyl group, a (n-hexylphenyl) methyl group, a (n-octylphenyl)methyl group, a (n-decylphenyl)methyl group, a (tetradecylphenyl) methyl group, a naphthylmethyl group and an anthracenylmethyl group.

The aralkyl group is preferably an aralkyl group having 7 to 20 carbon atoms, and more preferably a benzyl group.

As the aryl group, examples thereof include a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, a n-propylphenyl group, an isopropylphenyl group, a n-butylphenyl group, a sec-butylphenyl group, a tert-butylphenyl group, an isobutylphenyl group, a n-pentylphenyl group, a neopentylphenyl group, a n-hexylphenyl group, a n-octylphenyl group, a n-decylphenyl group, a n-dodecylphenyl group, a n-tetradecylphenyl group, a naphthyl group and an anthracenyl group.

The aryl group is preferably an aryl group having 6 to 20 carbon atoms, and more preferably a phenyl group.

These alkyl, aralkyl and aryl groups above-mentioned as $X^1$ to $X^4$, $R^{11}$ to $R^{16}$, $R^{21}$ to $R^{26}$, $R^{31}$ to $R^{36}$, $R^{41}$ to $R^{46}$ and $R^{51}$ to $R^{56}$ of the formula [4] to [6], maybe respectively substituted with a halogen atom such as a fluorine atom, a chlorine atom, a bromine atom or an iodine atom, an alkoxy group such as a methoxy group or an ethoxy group, an aryloxy group such as a phenoxy group, or an aralkyloxy group such as a benzyloxy group.

Further, as $X^1$ to $X^4$, $R^{11}$ to $R^{16}$, $R^{21}$ to $R^{26}$, $R^{31}$ to $R^{36}$, $R^{41}$ to $R^{46}$ and $R^{51}$ to $R^{56}$ of the formula [4] to [6], the substituted silyl group is a silyl group substituted with a hydrocarbon group, and the hydrocarbon group may be substituted with a halogen atom such as a fluorine atom, a chlorine atom, a bromine atom or an iodine atom; an alkoxy group such as a methoxy group or an ethoxy group; an aryloxy group such as a phenoxy group; or an aralkyloxy group such as benzyloxy group.

The hydrocarbon group preferably includes a alkyl groups having 1 to 20 carbon atoms such as a methyl group, an ethyl group, a n-propyl group, an isopropyl group, a n-butyl group, a sec-butyl group, a tert-butyl group, an isobutyl group, a n-pentyl group, a n-hexyl group, a cyclohexyl group and the like, and aryl groups having 6 to 20 carbon atoms such as a phenyl group, etc.

Examples of such substituted silyl group include mono-substituted silyl groups having 1 to 20 carbon atoms such as a methylsilyl group, an ethylsilyl group and a phenylsilyl group; di-substituted silyl groups having 2 to 20 carbon atoms such as a dimethylsilyl group, a diethylsilyl group and a diphenylsilyl group; and tri-substituted silyl groups having 3 to 20 carbon atoms such as a trimethylsilyl group, a triethylsilyl group, a tri-n-propylsilyl group, a triisopropylsilyl group, a tri-n-butylsilyl group, a tri-sec-butylsilyl group, a tri-tert-butylsilyl group, a tri-isobutylsilyl group, a tert-butyl-dimethylsilyl group, a tri-n-pentylsilyl group, a tri-n-hexylsilyl group, a tricyclohexylsilyl group and a triphenylsilyl group, and a trimethylsilyl group, a tert-butyldimethylsilyl group or a triphenylsilyl group is preferable.

The hydrocarbonoxy group in $X^1$ to $X^4$, $R^{11}$ to $R^{16}$, $R^{21}$ to $R^{26}$, $R^{31}$ to $R^{36}$, $R^{41}$ to $R^{46}$ and $R^{51}$ to $R^{56}$ of the formula [4] to [6], include an alkoxy group, aralkyloxy group, aryloxy group and the like.

Examples of the alkoxy group include a methoxy group, an ethoxy group, a n-propoxy group, an isopropoxy group, a n-butoxy group, a sec-butoxy group, a tert-butoxy group, a n-pentoxy group, a neopentoxy group, a n-hexoxy group, a n-octoxy group, a n-dodecoxy group, a n-pentadecoxy group and a n-eicosoxy group. These alkoxy groups may be partially substituted with a halogen atom such as a fluorine atom, a chlorine atom, a bromine atom or an iodine atom, an alkoxy group such as a methoxy group, an ethoxy group or the like, an aryloxy group such as a phenoxy group or the like or an aralkyloxy group such as a benzyloxy group or the like, etc.

The alkoxy group in $X^1$ to $X^4$, $R^{11}$ to $R^{16}$, $R^{21}$ to $R^{26}$, $R^{31}$ to $R^{36}$, $R^{41}$ to $R^{46}$ and $R^{51}$ to $R^{56}$ of the formulae [4] to [6], includes preferably an alkoxy group having 1 to 20 carbon atoms, more preferably a methoxy group, an ethoxy group, an isopropoxy group and a tert-butyl group.

Examples of the aralkyloxy group include a benzyloxy group, a (2-methylphenyl)methoxy group, a (3-methylphenyl)methoxy group, a (4-methylphenyl)methoxy group, a (2,3-dimethylphenyl)methoxy group, a (2,4-dimethylphenyl)methoxy group, a (2,5-dimethylphenyl)methoxy group, a (2,6-dimethylphenyl)methoxy group, a (3,4-dimethylphenyl)methoxy group, a (3,5-dimethylphenyl)methoxy group, a (2,3,4-trimethylphenyl)methoxy group, a (2,3,5-trimethylphenyl)methoxy group, a (2,3,6-trimethylphenyl)methoxy group, a (2,4,5-trimethylphenyl)methoxy group, a (2,4,6-trimethylphenyl)methoxy group, a (3,4,5-trimethylphenyl)methoxy group, a (2,3,4,5-tetramethylphenyl)methoxy group, a (2,3,4,6-tetramethylphenyl)methoxy group, a (2,3,5,6-tetramethylphenyl)methoxy group, a (pentamethylphenyl)methoxy group, an (ethylphenyl)methoxy group, a (n-propylphenyl)methoxy group, an (isopropylphenyl)methoxy group, (n-butylphenyl)methoxy group, a (sec-butylphenyl)methoxy group, a (tert-butylphenyl)methoxy group, a (n-hexylphenyl)methoxy group, a (n-octylphenyl)methoxy group, a (n-decylphenyl)methoxy group, a naphthylmethoxy group, an anthracenylmethoxy group.

These aralkyloxy groups may be substituted with a halogen atom such as a fluorine atom, a chlorine atom, a bromine atom or an iodine atom, an alkoxy group such as a methoxy group, an ethoxy group or the like, an aryloxy group such as a phenoxy group or the like or an aralkyloxy group such as a benzyloxy group or the like, etc.

The aralkyloxy group in $X^1$ to $X^4$, $R^{11}$ to $R^{16}$, $R^{21}$ to $R^{26}$, $R^{31}$ to $R^{36}$, $R^{41}$ to $R^{46}$ and $R^{51}$ to $R^{56}$ of the formulae [4] to [6], include preferably an aralkyloxy group having 7 to 20 carbon atoms, more preferably a benzyloxy group.

Examples of the aryloxy group include a phenoxy group, a 2-methylphenoxy group, a 3-methylphenoxy group, a 4-methylphenoxy group, a 2,3-dimethylphenoxy group, a 2,4-dimethylphenoxy group, a 2,5-dimethylphenoxy group, a 2,6-dimethylphenoxy group, a 3,4-dimethylphenoxy group, a 3,5-dimethylphenoxy group, a 2-tert-butyl-3-methylphenoxy group, a 2-tert-butyl-4-methylphenoxy group, a 2-tert-butyl-5-methylphenoxy group, a 2-tert-butyl-6-methylphenoxy group, a 2,3,4-trimethylphenoxy group, a 2,3,5-trimethylphenoxy group, a 2,3,6-trimethylphenoxy group, a 2,4,5-trimethylphenoxy group, a 2,4,6-trimethylphenoxy group, a 2-tert-butyl-3,4-dimethylphenoxy group, a 2-tert-butyl-3,5-dimethylphenoxy group, a 2-tert-butyl-3,6-dimethylphenoxy group, a 2,6-di-tert-butyl-3-methylphenoxy group, a 2-tert-butyl-4,5-dimethylphenoxy group, a 2,6-di-tert-butyl-4-methylphenoxy group, a 3,4,5-trimethylphenoxy group, a 2,3,4,5-tetramethylphenoxy group, a 2-tert-butyl-3,4,5-trimethylphenoxy group, a 2,3,4,6-tetramethylphenoxy group, a 2-tert-butyl-3,4,6-tetramethylphenoxy group, a 2-tert-butyl-3,4,6-trimethylphenoxy group, a 2,6-di-tert-butyl-3,4-dimethylphenoxy group, a 2,3,5,6-tetramethylphenoxy group, a 2-tert-butyl-3,5,6-trimethylphenoxy group, a 2,6-di-tert-butyl-3,5-dimethylphenoxy group, pentamethylphenoxy group, an ethylphenoxy group, a n-propylphenoxy group, an isopropylphenoxy group, a n-butylphenoxy group, a sec-butylphenoxy group, a tert-butylphenoxy group, a n-hexylphenoxy group, a n-octylphenoxy group, a n-decylphenoxy group, a n-tetradecylphenoxy group, a naphthoxy group and an anthracenoxy group.

These aryloxy groups may be substituted with a halogen atom such as a fluorine atom, a chlorine atom, a bromine atom or an iodine atom, an alkoxy group such as a methoxy group, an ethoxy group or the like, an aryloxy group such as a phenoxy group or the like or an aralkyloxy group such as a benzyloxy group or the like, etc.

The aryloxy group in $X^1$ to $X^4$, $R^{11}$ to $R^{16}$, $R^{21}$ to $R^{26}$, $R^{31}$ to $R^{36}$, $R^{41}$ to $R^{46}$ and $R^{51}$ to $R^{56}$ of the formulae [4] to [6], include preferably an aryloxy group having 6 to 20 carbon atoms.

The di-substituted amino group in $X^1$ to $X^4$, $R^{11}$ to $R^{16}$, $R^{21}$ to $R^{26}$, $R^{31}$ to $R^{36}$, $R^{41}$ to $R^{46}$ and $R^{51}$ to $R^{56}$ of the formula [4] to [6], is an amino group substituted with two hydrocarbon groups or silyl groups, and the hydrocarbon group and the silyl group may be substituted with a halogen atom such as a fluorine atom, a chlorine atom, a bromine atom or an iodine atom, an alkoxy group such as a methoxy group, an ethoxy group or the like, an aryloxy group such as a phenoxy group or the like or an aralkyloxy group such as a benzyloxy group or the like, etc.

Examples of the hydrocarbon group include alkyl groups having 1 to 20 carbon atoms such as a methyl group, an ethyl group, a n-propyl group, an isopropyl group, a n-butyl group, a sec-butyl group, a tert-butyl group, an isobutyl group, a n-pentyl group, a n-hexyl group and a cyclohexyl group; aryl groups having 6 to 10 carbon atoms such as a phenyl group; aralkyl groups having 7 to 10 carbon atoms such as a benzyl group, etc. The silyl group include, for example, a trimethylsilyl group, tert-butyldimethylsilyl group and the like. Examples of such di-substituted amino group include a dimethylamino group, a diethylamino group, a di-n-propylamino group, a diisopropylamino group, a di-n-butylamino group, a di-sec-butylamino group, a di-tert-butylamino group, a di-isobutylamino group, a tert-butylisopropylamino group, a di-n-hexylamino group, a di-n-octylamino group, a diphenylamino group, a bistrimethylsilylamino group, a bis-tert-butyldimethylsilylamino group and the like, and a dimethylamino group, a diethylamino group, a diisopropylamino group, a di-tert-butylamino group, a bis-trimethylsilylamino group are preferred.

The hydrocarbon thio group in $X^1$ to $X^4$, $R^{11}$ to $R^{16}$, $R^{21}$ to $R^{26}$, $R^{31}$ to $R^{36}$, $R^{41}$ to $R^{46}$ and $R^{51}$ to $R^{56}$ of the formula [4] to [6], includes an alkylthio group, an aralkylthio grouo, arylthio group.

Examples of the alkylthio group include a methylthio group, an ethylthio group, a n-propylthio group, an isopropylthio group, a n-butylthio group, a sec-butylthio group, a tert-butylthio group, a n-pentylthio group, a neopentylthio group, a n-hexylthio group, a n-octylthio group, a n-dodecylthio group, a n-pentadecylthio group and a n-eicosylthio group.

The alkylthio group is preferably an alkylthio group having 1 to 20 carbon atoms, and more preferably a methylthio group, an ethylthio group, an isopropylthio group or a tert-butylthio group.

Examples of the aralkylthio group include a benzylthio group, a (2-methylphenyl)methylthio group, a (3-methylphenyl)methylthio group, a (4-methylphenyl)methylthio group, a (2,3-dimethylphenyl)methylthio group, a (2,4-dimethylphenyl)methylthio group, a (2,5-dimethylphenyl)methylthio group, a (2,6-dimethylphenyl)methylthio group, a (3,4-dimethylphenyl)methylthio group, a (3,5-dimethylphenyl)methylthio group, a (2,3,4-timethylphenyl)methylthio group, a (2,3,5-timethylphenyl)methylthio group, a (2,3,6-timethylphenyl)methylthio group, a (2,4,5-timethylphenyl)methylthio group, a (2,4,6-timethylphenyl)methylthio group, a (3,4,5-timethylphenyl)methylthio group, a (2,3,4,5-tetramethylphenyl)methylthio group, a (2,3,4,6-tetramethylphenyl)methylthio group, a (2,3,5,6-tetramethylphenyl)methylthio group, a (pentamethylphenyl)methylthio group, an (ethylphenyl)methylthio group, a (n-propylphenyl)methylthio group, an (isopropylphenyl)methylthio group, a (n-butylphenyl)methylthio group, a (sec-butylphenyl)methylthio group, a (tert-butylphenyl)methylthio group, a (n-hexylphenyl)methylthio group, a (n-octylphenyl)methylthio group, a (n-decylphenyl)methylthio group, a naphthylmethylthio group, an anthracenylmethylthio group and the like.

The aralkylthio group is preferably an aralkylthio group having 7 to 20 carbon atoms, and more preferably a benzylthio group, and a benzylthio group is more preferable.

Examples of the arylthio group include a phenylthio group, a 2-methyphenylthio group, a 3-methylphenylthio group, a 4-methylphenylthio group, a 2,3-dimethylphenylthio group, a 2,4-dimethylphenylthio group, a 2,5-dimethylphenylthio group, a 2,6-dimethylphenylthio group, a 3,4-dimethylphenylthio group, a 3,5-dimethylphenylthio group, a 2-tert-butyl-3-methylphenylthio group, a 2-tert-butyl-4-methylphenylthio group, a 2-tert-butyl-5-methylphenylthio group, a 2-tert-butyl-6-methylphenylthio group, a 2,3,4-trimethylphenylthio group, a 2,3,5-trimethylphenylthio group, a 2,3,6-trimethylphenylthio group, a 2,4,5-trimethylphenylthio group, a 2,4,6-trimethylphenylthio group, a 2-tert-butyl-3,4-dimethylphenylthio group, a 2-tert-butyl-3,5-dimethylphenylthio group, a 2-tert-butyl-3,6-dimethylphenylthio group, a 2,6-di-tert-butyl-3-methylphenylthio group, a 2-tert-butyl-4,5-dimethylphenylthio group, a 2,6-di-tert-butyl-4-methylphenylthio group, a 3,4,5-trimethylphenylthio group, a 2,3,4,5-tetramethylphenylthio group, a 2,3,4,6-tetramethylphenylthio group, a 2-tert-butyl-3,4,6-trimethylphenylthio group, a 2,6-di-tert-butyl-3,4-dimethylphenylthio group, a 2,3,5,6-tetramethylphenylthio group, a 2-tert-butyl-3,5,6-trimethylphenylthio group, a 2,6-di-tert-butyl-3,5-dimethylphenylthio group, a pentamethylphenylthio group, an ethylphenylthio group, a n-propylphenylthio group, an isopropylphenylthio group, a n-butylphenylthio group, a sec-butylphenylthio group, a tert-butylphenylthio group, a n-pentylphenylthio group, a neopentylphenylthio group, a n-hexylphenylthio group, a n-octylphenylthio group, a n-decylphenylthio group, a n-tetradecylphenylthio group, a naphthylthio group, an anthracenylthio group and the like.

The arylthio group is preferably an arylthio group having 6 to 20 carbon atoms.

Further, these alkylthio, aralkylthio and arylthio groups above-mentioned may be respectively substituted with a halogen atom such as a fluorine atom, a chlorine atom, a bromine atom or an iodine atom, an alkoxy group such as a methoxy group, an ethoxy group or the like, an aryloxy group such as a phenoxy group or the like or an aralkyloxy group such as a benzyloxy group or the like.

The hydrocarbon seleno group in $X^1$ to $X^4$, $R^{11}$ to $R^{16}$, $R^{21}$ to $R^{26}$, $R^{31}$ to $R^{36}$, $R^{41}$ to $R^{46}$ and $R^{51}$ to $R^{56}$ of the formula [4] to [6], includes an alkylseleno group, an aralkylseleno grouo, arylseleno group.

Examples of the alkylseleno group include a methylseleno group, an ethylseleno group, a n-propylseleno group, an isopropylseleno group, a n-butylseleno group, a sec-butylseleno group, a tert-butylseleno group, a n-pentylseleno group, a neopentylseleno group, a n-hexylseleno group, a n-octylseleno group, a n-dodecylseleno group, a n-pentadecylseleno group, a n-eicosylseleno group and the like.

The alkylseleno group is preferably an alkylseleno group having 1 to 20 carbon atoms, and more preferably a methylseleno group, an ethylseleno group, an isopropylseleno group or a tert-butylseleno group.

The examples of the aralkylseleno group include a benzylseleno group, a (2-methylphenyl)methylseleno group, a (3-methylphenyl)methylseleno group, a (4-methylphenyl)methylseleno group, a (2,3-dimethylphenyl)methylseleno group, a (2,4-dimethylphenyl)methylseleno group, a (2,5-dimethylphenyl)methylseleno group, a (2,6-dimethylphenyl)methylseleno group, a (3,4-dimethylphenyl)methylseleno group, a (3,5-dimethylphenyl)methylseleno group, a (2,3,4-timethylphenyl)methylseleno group, a (2,3,5-timethylphenyl)methylseleno group, a (2,3,6-timethylphenyl)methylseleno group, a (2,4,5-timethylphenyl)methylseleno group, a (2,4,6-timethylphenyl)methylseleno group, a (3,4,5-timethylphenyl)methylseleno group, a (2,3,4,5-tetramethylphenyl)methylseleno group, a (2,3,4,6-tetramethylphenyl)methylseleno group, a (2,3,5,6-tetramethylphenyl)methylseleno group, a (pentamethylphenyl)methylseleno group, an (ethylphenyl)methylseleno group, a (n-propylphenyl)methylseleno group, an (isopropylphenyl)methylseleno group, a (n-butylphenyl)methylseleno group, a (sec-butylphenyl)methylseleno group, a (tert-butylphenyl)methylseleno group, a (n-hexylphenyl)methylseleno group, a (n-octylphenyl)methylseleno group, a (n-decylphenyl)methylseleno group, a naphthylmethylseleno group, an anthracenylmethylseleno group and the like.

The aralkylseleno group is preferably an aralkylseleno group having 7 to 20 carbon atoms, and more preferably a benzylseleno group.

Examples of the arylseleno group include a phenylseleno group, a 2-methylphenylseleno group, a 3-methylphenylseleno group, a 4-methylphenylseleno group, a 2,3-dimethylphenylseleno group, a 2,4-dimethylphenylseleno group, a 2,5-dimethylphenylseleno group, a 2,6-dimethylphenylseleno group, a 3,4-dimethylphenylseleno group, a 3,5-dimethylphenylseleno group, a 2-tert-butyl-3-methylphenylseleno group, a 2-tert-butyl-4-methylphenylseleno group, a 2-tert-butyl-5-methylphenylseleno group, a 2-tert-butyl-6-methylphenylseleno group, a 2,3,4-trimethylphenylseleno group, a 2,3,5-trimethylphenylseleno group, a 2,3,6-trimethylphenylseleno group, a 2,4,5-trimethylphenylseleno group, a 2,4,6-trimethylphenylseleno group, a 2-tert-butyl-3,4-dimethylphenylseleno group, a 2-tert-butyl-3,5-dimethylphenylseleno group, a 2-tert-butyl-3,6-dimethylphenylseleno group, a 2,6-di-tert-butyl-3-methylphenylseleno group, a 2-tert-butyl-4,5-dimethylphenylseleno group, a 2,6-di-tert-butyl-4-methylphenylseleno group, a 3,4,5-trimethylphenylseleno group, a 2,3,4,5-tetramethylphenylseleno group, a 2,3,4,6-tetramethylphenylseleno group, a 2-tert-butyl-3,4,6-trimethylphenylseleno group, a 2,6-di-tert-butyl-3,4-dimethylphenylseleno group, a 2,3,5,6-tetramethylphenylseleno group, a 2-tert-butyl-3,5,6-trimethylphenylseleno group, a 2,6-di-tert-butyl-3,5-dimethylphenylseleno group, a pentamethylphenylseleno group, an ethylphenylseleno group, a n-propylphenylseleno group, an isopropylphenylseleno group, a n-butylphenylseleno group, a sec-butylphenylseleno group, a tert-butylphenylseleno group, a n-pentylphenylseleno group, a neopentylphenylseleno group, a n-hexylphenylseleno group, a n-octylphenylseleno group, a n-decylphenylseleno group, a n-tetradecylphenylseleno group, a naphthylseleno group, an anthracenylseleno group and the like.

The arylseleno group is preferably an alkylseleno group having 6 to 20 carbon atoms.

These alkylseleno, aralkylseleno and arylseleno groups above-mentioned may be respectively substituted with a halogen atom such as a fluorine atom, a chlorine atom, a bromine atom or an iodine atom, an alkoxy group such as a methoxy group, an ethoxy group or the like, an aryloxy group such as a phenoxy group or the like or an aralkyloxy group such as a benzyloxy group or the like.

$X^1$ to $X^4$ in the formula [4] to [6] are preferably independently a halogen atom, an alkyl group, an aralkyl group, an alkoxy group, an aryloxy group or a di-substituted amino group, and more preferably a halogen atom, an alkyl group, an alkoxy group or an aryloxy group.

Further, $R^{11}$ to $R^{14}$, $R^{21}$ to $R^{24}$, $R^{31}$ to $R^{34}$, $R^{41}$ to $R^{44}$ and $R^{51}$ to $R^{54}$ in the formula [4] to [6], are preferably independently a hydrogen atom, a halogen atom, an alkyl group, an aralkyl group, an aryl group, a substituted silyl group, an alkoxy group, an aralkyloxy group or an aryloxy group, and particularly, $R^{11}$, $R^{21}$, $R^{31}$, $R^{41}$ and $R^{51}$ are preferably independently an alkyl group, an aralkyl group, an aryl group or a substituted silyl group.

Furthermore, $R^{15}$, $R^{16}$, $R^{25}$, $R^{26}$, $R^{35}R^{36}$, $R^{45}$, $R^{46}$, $R^{55}$ and $R^{56}$ are preferably independently a hydrogen atom, an alkyl group, an aralkyl group, an aryl group, a substituted silyl group, an alkoxy group, an aralkyloxy group or an aryloxy group.

Moreover, $X^5$ to $X^7$ in the formula [5] and [6], represent an atom of Group 16 of the periodic table of the elements such as an oxygen atom, a sulfur atom or a selenium atom, and are preferably an oxygen atom or a sulfur atom, more preferably an oxygen atom.

Furthermore, $A^1$ to $A^5$ in the formula [4] to [6], represent an atom of Group 16 of the periodic table of the elements such as an oxygen atom, a sulfur atom or a selenium atom, and are preferably an oxygen atom.

Moreover, $J^1$ to $J^5$ in the formula [4] to [6], represent an atom of Group 14 of the periodic table of the elements such as a carbon atom, a silicon atom or a germanium atom, and are preferably a carbon atom or a silicon atom.

Examples of the metal compound represented by the formula [4] include methylene($\eta^5$-cyclopentadienyl) (3,5-dimethyl-2-phenoxy)titanium dichloride (herein-after, "$\eta^5$-" is sometimes omitted), methylene(cyclopentadienyl)(3-tert-butyl-2-phenoxy)titanium dichloride, methylene(cyclopentadienyl)(3-tert-butyl-5-methyl-2-phenoxy)titanium dichloride, methylene(cyclopentadienyl)(3-phenyl-2-phenoxy) titanium dichloride, methylene(cyclopentadienyl)(3-tert-butyldimethylsilyl-5-methyl-2-phenoxy)titanium dichloride, methylene(cyclopentadienyl)(3-trimethylsilyl-5-methyl-2-phenoxy)titanium dichloride, methylene(cyclopentadienyl)(3-tert-butyl-5-methoxy-2-phenoxy)titanium dichloride, methylene(cyclopentadienyl)(3-tert-butyl-5-chloro-2-phenoxy)titanium dichloride, methylene(tetramethylcyclopentadienyl)(3,5-dimethyl-2-phenoxy)titanium dichloride, methylene(tetramethylcyclopentadienyl)(3-tert-butyl-2-phenoxy)titanium dichloride, methylene(tetramethylcyclopentadienyl)(3-tert-butyl-5-methyl-2-phenoxy)titanium dichloride, methylene(tetramethylcyclopentadienyl) (3-phenyl-2-phenoxy)titanium dichloride, methylene (tetramethylcyclopentadienyl)(3-tert-butyldimethylsilyl-5-methyl-2-phenoxy)titanium dichloride, methylene (tetramethylcyclopentadienyl) (3-trimethylsilyl-5-methyl-2-phenoxy)titanium dichloride, methylene (tetramethylcyclopentadienyl) (3-tert-butyl-5-methoxy-2-phenoxy)titanium dichloride, methylene (tetramethylcyclopentadienyl) (3-tert-butyl-5-chloro-2-phenoxy)titanium dichloride, isopropylidene (cyclopentadienyl)(3,5-dimethyl-2-phenoxy)titanium dichloride, isopropylidene(cyclopentadienyl)(3-tert-butyl-2-phenoxy)titanium dichloride, isopropylidene(cyclopentadienyl)(3-tert-butyl-5-methyl-2-phenoxy)titanium dichloride, isopropylidene(cyclopentadienyl)(3-phenyl-2-phenoxy)titanium dichloride, isopropylidene(cyclopentadienyl)(3-tert-butyldimethylsilyl-5-methyl-2-phenoxy)titanium dichloride, isopropylidene(cyclopentadienyl)(3-trimethylsilyl-5-methyl-2-phenoxy)titanium dichloride, isopropylidene (cyclopentadienyl)(3-tert-butyl-5-methoxy-2-phenoxy) titanium dichloride, isopropylidene(cyclopentadienyl)(3-tert-butyl-5-chloro-2-phenoxy)titanium dichloride, isopropylidene(tetramethylcyclopentadienyl)(3,5-dimethyl-2-phenoxy)titanium dichloride, isopropylidene(tetramethylcyclopentadienyl)(3-tert-butyl-2-phenoxy)titanium dichloride, isopropylidene(tetramethylcyclopentadienyl)(3-tert-butyl-5-methyl-2-phenoxy)titanium dichloride, isopropylidene(tetramethylcyclopentadienyl)(3-phenyl-2-phenoxy)titanium dichloride, isopropylidene(tetramethylcyclopentadienyl)(3-tert-butyldimethylsilyl-5-methyl-2-phenoxy)titanium dichloride, isopropylidene (tetramethylcyclopentadienyl) (3-trimethylsilyl-5-methyl-2-phenoxy)titanium dichloride, isopropylidene (tetramethylcyclopentadienyl)(3-tert-butyl-5-methoxy-2-phenoxy)titanium dichloride, isopropylidene (tetramethylcyclopentadienyl)(3-tert-butyl-5-chloro-2-phenoxy)titanium dichloride, diphenylmethylene (cyclopentadienyl)(3,5-dimethyl-2-phenoxy)titanium dichloride, diphenylmethylene(cyclopentadienyl)(3-tert-butyl-2-phenoxy)titanium dichloride, diphenylmethylene(cyclopentadienyl)(3-tert-butyl-5-methyl-2-phenoxy)titanium dichloride, diphenylmethylene(cyclopentadienyl)(3-phenyl-2-phenoxy)titanium dichloride, diphenylmethylene(cyclopentadienyl)(3-tert-butyldimethylsilyl-5-methyl-2-phenoxy)titanium dichloride, diphenylmethylene (cyclopentadienyl)(3-trimethylsilyl-5-methyl-2-phenoxy) titanium dichloride, diphenylmethylene(cyclopentadienyl) (3-tert-butyl-5-methoxy-2-phenoxy)titanium dichloride, diphenylmethylene(cyclopentadienyl)(3-tert-butyl-5-chloro-2-phenoxy)titanium dichloride, diphenylmethylene (tetramethylcyclopentadienyl)(3,5-dimethyl-2-phenoxy)titanium dichloride, diphenylmethylene (tetramethylcyclopentadienyl)(3-tert-butyl-2-phenoxy) titanium dichloride, diphenylmethylene (tetramethylcyclopentadienyl)(3-tert-butyl-5-methyl-2-phenoxy)titanium dichloride, diphenylmethylene (tetramethylcyclopentadienyl)(3-phenyl-2-phenoxy) titanium dichloride, diphenylmethylene (tetramethylcyclopentadienyl)(3-tert-butyldimethylsilyl-5-methyl-2-phenoxy)titanium dichloride, diphenylmethylene (tetramethylcyclopentadienyl)(3-trimethylsilyl-5-methyl-2-phenoxy)titanium dichloride, diphenylmethylene (tetramethylcyclopentadienyl)(3-tert-butyl-5-methoxy-2-phenoxy)titanium dichloride, diphenylmethylene (tetramethylcyclopentadienyl)(3-tert-butyl-5-chloro-2- phenoxy)titanium dichloride, and compounds in which ($\eta^5$-cyclopentadienyl) in the above-mentioned compounds is replaced with ($\eta^5$-methylcyclopentadienyl), ($\eta^5$-dimethylcyclopentadienyl), ($\eta^5$-trimethylcyclopentadienyl), ($\eta^5$-n-butylcyclopentadienyl), ($\eta^5$-tert-butylcyclopentadienyl), ($\eta^5$-trimethylsilylcyclopentadienyl), ($\eta^5$-tert-butyldimethylsilylcyclopentadienyl), ($\eta^5$-indenyl), ($\eta^5$-phenylindenyl) or ($\eta^5$-fluorenyl).

Further, compounds in which dichloride in the above-mentioned compounds is replaced with dimethyl, dibenzyl, dimethoxide, diphenoxide, bis(dimethylamino) or bis(diethylamino) are also exemplified.

Moreover, examples of the metal compound represented by the formula [4] include Dimethylsilylene ($\eta^5$-cyclopentadienyl)(2-phenoxy)titanium dichloride, dimethylsilylene ($\eta^5$-cyclopentadienyl)(3-methyl-2-phenoxy)titanium dichloride, dimethylsilylene($\eta^5$-cyclopentadienyl)(3,5-dimethyl-2-phenoxy)titanium dichloride, dimethylsilylene($\eta^5$-cyclopentadienyl)(3-tert-butyl-2-phenoxy)titanium dichloride, dimethylsilylene($\eta^5$-cyclopentadienyl)(3-tert-butyl-5-methyl-2-phenoxy)titanium dichloride, dimethylsilylene ($\eta^5$-cyclopentadienyl)(3,5-di-tert-butyl-2-phenoxy)titanium dichloride, dimethylsilylene($\eta^5$-cyclopentadienyl)(5-methyl-3-phenyl-2-phenoxy)titanium dichloride, dimethylsilylene($\eta^5$-cyclopentadienyl)(3-tert-butyldimethylsilyl-5-methyl-2-phenoxy)titanium dichloride, dimethylsilylene ($\eta^5$-cyclopentadienyl)(5-methyl-3-trimethylsilyl-2-phenoxy)titanium dichloride, dimethylsilylene($\eta^5$-cyclopentadienyl)(3-tert-butyl-5-methoxy-2-phenoxy) titanium dichloride, dimethylsilylene($\eta^5$-cyclopentadienyl) (3-tert-butyl-5-chloro-2-phenoxy)titanium dichloride, dimethylsilylene($\eta^5$-cyclopentadienyl)(3,5-diamyl-2-phenoxy)titanium dichloride, dimethylsilylene($\eta^5$-cyclopentadienyl)(1-naphtoxy-2-yl)titanium dichloride, dimethylsilylene($\eta^5$-tetramethylcyclopentadienyl)(2-phenoxy) titanium dichloride, dimethylsilylene($\eta^5$-tetramethylcyclopentadienyl)(3-methyl-2-phenoxy)titanium dichloride, dimethylsilylene($\eta^5$-tetramethylcyclopentadienyl)(3,5-dimethyl-2-phenoxy)titanium dichloride, dimethylsilylene($\eta^5$-tetramethylcyclopentadienyl)(3-tert-butyl-2-phenoxy)titanium dichloride, dimethylsilylene($\eta^5$-tetramethylcyclopentadienyl)(3-tert-butyl-5-methyl-2-phenoxy)titanium dichloride, dimethylsilylene($\eta^5$-tetramethylcyclopentadienyl)(3,5-di-tert-butyl-2-phenoxy) titanium dichloride, dimethylsilylene($\eta^5$-tetramethylcyclopentadienyl)(5-methyl-3-phenyl-2-phenoxy)titanium dichloride, dimethylsilylene($\eta^5$-tetramethylcyclopentadienyl)(3-tert-butyldimethylsilyl-5-methyl-2-phenoxy)titanium dichloride, dimethylsilylene ($\eta^5$-tetramethylcyclopentadienyl)(5-methyl-3-trimethylsilyl-2-phenoxy)titanium dichloride, dimethylsilylene($\eta^5$-tetramethylcyclopentadienyl)(3-tert-butyl-5-methoxy-2-phenoxy)titanium dichloride, dimethylsilylene($\eta^5$-tetramethylcyclopentadienyl)(3-tert-butyl-5-chloro-2-phenoxy)titanium dichloride, dimethylsilylene($\eta^5$-tetramethylcyclopentadienyl)(3,5-diamyl-2-phenoxy) titanium dichloride, dimethylsilylene($\eta^5$-cyclopentadienyl) (1-naphtoxy-2-yl)titanium dichloride, compounds in which ($\eta^5$-cyclopentadienyl) in the above-mentioned compounds is peplaced with ($\eta^5$-methylcyclopentadienyl), ($\eta^5$-dimethylcyclopentadienyl), ($\eta^5$-trimethylcyclopentadienyl), ($\eta^5$-n-butylcyclopentadienyl), ($\eta^5$-tert-butylcyclopentadienyl), ($\eta^5$-trimethylsilylcyclopentadienyl), ($\eta^5$-tert-butyldimethylsilylcyclopentadienyl), ($\eta^5$-indenyl), ($\eta^5$-phenylindenyl) or ($\eta^5$-fluorenyl), compounds in which (2-phenoxy) in the above-mentioned compounds is replaced with with 3-phenyl-2-phenoxy, 3-trimethylsilyl-2-phenoxy or 3-tert-butyldimethylsilyl-2-phenoxy, and compounds in which dimethylsilylene in the above-mentioned compounds is replaced with diethysilylene, diphenylsilylene or dimethoxysilylene. Further, compounds in which dichloride in the above-mentioned compounds is replaced with dimethyl, dibenzyl, dimethoxide, diphenoxide, bis (dimethylamino) or bis(diethylamino) are also exemplified. Furthermore, compounds in which titanium in the above-mentioned compounds is replaced with zirconium or hafnium are exemplified.

Moreover, in the metal compounds represented by the formula[5], specific examples of μ-oxo type compounds include μ-oxobis{isopropylidene(cyclopentadienyl) (2-phenoxy)titanium chloride}, μ-oxobis{isopropylidene(cyclopentadienyl)(2-phenoxy)titanium methoxide}, μ-oxobis{isopropylidene (cyclopentadienyl)(3-tert-butyl-5-methyl-2-phenoxy)titanium chloride}, μ-oxobis{isopropylidene (cyclopentadienyl) (3-tert-butyl-5-methyl-2-phenoxy) titanium methoxide}, μ-oxobis{isopropylidene (methylcyclopentadienyl)(2-phenoxy)titanium chloride}, μ-oxobis{isopropylidene (methylcyclopentadienyl) (2-phenoxy)titanium methoxide}, μ-oxobis{isopropylidene(methylcyclopentadienyl) (3-tert-butyl-5-methyl-2-phenoxy)titanium chloride}, μ-oxobis{isopropylidene(methylcyclopentadienyl) (3-tert-butyl-5-methyl-2-phenoxy)titanium methoxide}, μ-oxobis{isopropylidene(tetramethylcyclopentadienyl) (2-phenoxy)titanium chloride}, μ-oxobis{isopropylidene (tetramethylcyclopentadienyl) (2-phenoxy)titanium methoxide}, μ-oxobis{isopropylidene(tetramethylcyclopentadienyl) (3-tert-butyl-5-methyl-2-phenoxy)titanium chloride}, μ-oxobis{isopropylidene(tetramethylcyclopentadienyl) (3-tert-butyl-5-methyl-2-phenoxy)titanium methoxide} and compounds in which ($\eta^5$-cyclopentadienyl) in the above-mentioned compouns is replaced with ($\eta^5$-dimethylcyclopentadienyl), ($\eta^5$-trimethylcyclopentadienyl), ($\eta^5$-n-butyl-cyclopentadienyl), ($\eta^5$-tert-butylcyclopentadienyl), ($\eta^5$-trimethylsilylcyclopentadienyl), ($\eta^5$-tert-butyldimethylsilylcyclopentadienyl), ($\eta^5$-indenyl), ($\eta^5$-methylindenyl) or ($\eta^5$-fluorenyl). Further, compounds in which (2-phenoxy) in the above-mentioned compounds is replaced with with (3-methyl-2-phenoxy), (3,5-dimethyl-2-phenoxy), (3,5-di-tert-butyl-2-phenoxy), (3-phenyl-5-methyl-2-phenoxy) or (3-trimethylsilyl-5-methyl-2-phenoxy) and compounds in which chloride in the above-mentioned compounds is replaced with methyl, benzyl, phenoxide, dimethylamino or diethylamino are also exemplified. Furthermore, compounds in which titanium in the above-mentioned compounds is replaced with zirconium or hafnium are exemplified.

Moreover, in the metal compounds represented by the formula[6], specific examples of μ-oxo type compounds include di-μ-oxobis[isopropylidene(cyclopentadienyl) (2-phenoxy)titanium], di-μ-oxobis[isopropylidene(cyclopentadienyl) (3-tert-butyl-5-methyl-2-phenoxy)titanium], di-μ-oxobis[isopropylidene(methylcyclopentadienyl) (2-phenoxy) titanium], di-μ-oxobis[isopropylidene(methylcyclopentadienyl) (3-tert-butyl-5-methyl-2-phenoxy)titanium], di-μ-oxobis[isopropylidene (tetramethylcyclopentadienyl)(2-phenoxy)titanium], di-μ-oxobis[isopropylidene (tetramethylcyclopentadienyl)(3-tert-butyl-5-methyl-2-phenoxy)titanium], di-μ-oxobis [dimethylsilylene(cyclopentadienyl)(2-phenoxy)titanium], di-μ-oxobis[dimethylsilylene (cyclopentadienyl) (3-tert-butyl-5-methyl-2-phenoxy) titanium], di-μ-oxobis[dimethylsilylene (methylcyclopentadienyl) (2-phenoxy)titanium], di-μ-oxobis[dimethylsilylene(methylcyclopentadienyl) (3-tert-butyl-5-methyl-2-phenoxy)titanium], di-μ-oxobis

[dimethylsilylene(tetramethylcyclopentadienyl) (2-phenoxy)titanium], di-μ-oxobis[dimethylsilylene(tetramethylcyclopentadienyl) (3-tert-butyl-5-methyl-2-phenoxy)titanium] and compounds in which ($\eta^5$-cyclopentadienyl) in the above-mentioned compouns is replaced with ($\eta^5$-dimethylcyclopentadienyl), ($\eta^5$-trimethylcyclopentadienyl), ($\eta^5$-n-butylcyclopentadienyl), ($\eta^5$-tert-butylcyclopentadienyl), ($\eta^5$-trimethylsilylcyclopentadienyl), ($\eta^5$-tert-butyldimethylsilylcyclopentadienyl), ($\eta^5$-indenyl), ($\eta^5$-methylindenyl) or ($\eta^5$-fluorenyl). Further, compounds in which (2-phenoxy) in the above-mentioned compounds is replaced with with (3-methyl-2-phenoxy), (3,5-dimethyl-2-phenoxy), (3,5-di-tert-butyl-2-phenoxy), (3-phenyl-5-methyl-2-phenoxy) or (3-trimethylsilyl-5-methyl-2-phenoxy). Furthermore, compounds in which titanium in the above-mentioned compounds is replaced with zirconium or hafnium are exemplified.

As the organoaluminum compound (C) which is a component used for the catalyst for addition polymerization of the present invention, known organoaluminum compounds can be used. The organoaluminum compound indicated by the formula [12] described below is preferable.

$$R^{18}{}_d AlY_{3-d} \quad [12]$$

(wherein $R^{18}$ represents a hydrocarbon group, and when $R^{18}$ exists more than one, $R^{18}$'s may be the same or different; Y represents a hydrogen atom, a halogen atom, an hydrocarbonoxy group, and Y exists more than one, Y's may be the same or different; and "d" represents a numeral satisfying $0<d\leq 3$.)

$R^{18}$ in the formula [12] is preferably a hydrocarbon group having 1 to 24 carbon atoms, and more preferably an alkyl group having 1 to 24 carbon atoms. Specific examples thereof include a methyl group, an ethyl group, a n-propyl group, a n-butyl group, an isobutyl group, a n-hexyl group, a 2-methylhexyl group and a n-octyl group, and an ethyl group, a n-butyl group, an isobutyl group or a n-hexyl group is more preferable.

Further, specific example of a case in which Y is a halogen atom includes a fluorine atom, a chlorine atom, a bromine atom and an iodine atom, and a chlorine atom is preferable.

The hydrocarbonoxy group in Y is preferably an alkoxy group, an aralkyloxy group and an aryloxy group.

Specific examples of the alkoxy group include a methoxy group, an ethoxy group, a n-propoxy group, an isopropoxy group, a n-butoxy group, a sec-butoxy group, a tert-butoxy group, a n-pentoxy group, a neopentoxy group, a n-hexoxy group, a n-octoxy group, a n-dodecoxy group, a n-pentadecoxy group and a n-eicosoxy group. Any one of these alkoxy, aryloxy and aralkyloxy groups above-mentioned may be substituted with a halogen atom such as a fluorine atom, a chlorine atom, a bromine atom, an iodine atom or the like, an alkoxy group such as a methoxy group, an ethoxy group or the like, or an aryloxy group such as a phenoxy group or the like.

The alkoxy group is preferably an alkoxy group having 1 to 24 carbon atoms and a methoxy group, an ethoxy group and a tert-butoxy group are more preferred.

Specific examples of the aryloxy group in Y include a phenoxy group, a 2-methylphenoxy group, a 3-methylphenoxy group, a 4-methylphenoxy group, a 2,3-dimethylphenoxy group, a 2,4-dimethylphenoxy group, a 2,5-dimethylphenoxy group, a 2,6-dimethylphenoxy group, a 3,4-dimethylphenoxy group, a 3,5-dimethylphenoxy group, a 2,3,4-trimethylphenoxy group, a 2,3,5-trimethylphenoxy group, a 2,3,6-trimethylphenoxy group, a 2,4,5-trimethylphenoxy group, a 2,4,6-trimethylphenoxy group, a 3,4,5-trimethylphenoxy group, a 2,3,4,5-tetramethylphenoxy group, a 2,3,4,6-tetramethylphenoxy group, 2,3,5,6-tetramethylphenoxy group, a pentamethylphenoxy group, an ethylphenoxy group, a n-propylphenoxy group, an isopropylphenoxy group, a n-butylphenoxy group, a sec-butylphenoxy group, a tert-butylphenoxy group, a n-hexylphenoxy group, a n-octylphenoxy group, a n-decylphenoxy group, a n-tetradecylphenoxy group, a naphthoxy group and an anthrathenoxy group. The aryloxy group is preferably an aryloxy group having 6 to 24 carbon atoms.

Examples of the aralkyloxy group in Y include a benzyloxy group, a (2-methylphenyl)methoxy group, a (3-methylphenyl)methoxy group, a (4-methylphenyl)methoxy group, a (2,3-dimethylphenyl)methoxy group, a (2,4-dimethylphenyl)methoxy group, a (2,5-dimethylphenyl)methoxy group, a (2,6-dimethylphenyl)methoxy group, a (3,4-dimethylphenyl)methoxy group, a (3,5-dimethylphenyl)methoxy group, a (2,3,4-trimethylphenyl)methoxy group, a (2,3,5-trimethylphenyl)methoxy group, a (2,3,6-trimethylphenyl)methoxy group, a (2,4,5-trimethylphenyl)methoxy group, a (2,4,6-trimethylphenyl)methoxy group, a (3,4,5-trimethylphenyl)methoxy group, a (2,3,4,5-tetramethylphenyl)methoxy group, a (2,3,4,6-tetramethylphenyl)methoxy group, a (2,3,5,6-tetramethylphenyl)methoxy group, a (pentamethylphenyl)methoxy group, an (ethylphenyl)methoxy group, a (n-propylphenyl)methoxy group, an (isopropylphenyl)methoxy group, a (n-butylphenyl)methoxy group, a (sec-butylphenyl)methoxy group, a (tert-butylphenyl)methoxy group, a (n-hexylphenyl)methoxy group, a (n-octylphenyl)methoxy group, a (n-decylphenyl)methoxy group, a (n-tetradecylphenyl)methoxy group, a naphthylmethoxy group and an anthrathenylmethoxy group.

The aralkyloxy group is preferably an aralkyloxy group having 7 to 24 carbon atoms, and s a benzyloxy group is more preferred.

Any one of these alkoxy, aryloxy and aralkyloxy groups above-mentioned may be substituted with a halogen atom such as a fluorine atom, a chlorine atom, a bromine atom, an iodine atom or the like, an alkoxy group such as a methoxy group, an ethoxy group or the like, or an aryloxy group such as a phenoxy group or the like.

Specific examples of the organoaluminum compound represented by the formula [12] include trialkylaluminums such as trimethylaluminum, triethylaluminum, tri-n-propylaluminum, tri-n-butylaluminum, triisobutylaluminum, tri-n-hexylaluminum, tri-n-octylaluminum and the like; dialkylaluminum chlorides such as dimethylaluminum chloride, diethylaluminum chloride, di-n-propylaluminum chloride, di-n-butylaluminum chloride, diisobutylaluminum chloride, di-n-hexylaluminum chloride and the like; alkylaluminum dichlorides such as methylaluminum dichloride, ethylaluminum dichloride, n-propylaluminum dichloride, n-butylaluminum dichloride, isobutylaluminum dichloride, n-hexylaluminum dichloride and the like; dialkylaluminum hydrides such as dimethylaluminum hydride, diethylaluminum hydride, di-n-propylaluminum hydride, di-n-butylaluminum hydride, diisobutylaluminum hydride, di-n-hexylaluminum hydride and the like, alkyl(dialkoxy)aluminums such as methyl(dimethoxy)aluminum, methyl(diethoxy)aluminum, methyl(di-tert-butoxy)aluminum and the like; dialkyl(alkoxy)aluminums such as dimethyl(methoxy)aluminum, dimethyl(ethoxy)aluminum, dimethyl(tert-butoxy)aluminum and the like; alkyl(diaryloxy)aluminums such as methyl (diphenoxy)aluminum, methylbis(2,6-diisopropylphenoxy) aluminum, methylbis(2,6-diphenylphenoxy)aluminum and the like; dialkyl(aryloxy)aluminums such as dimethyl(phenoxy)aluminum, dimethyl(2,6-diisopropylphenoxy)aluminum, dimethyl(2,6-diphenylphenoxy)aluminum and the like, etc.

Among these, a trialkylaluminum is preferable, and trimethylaluminum, triethylaluminum, tri-n-butylaluminum, triisobutylaluminum or tri-n-hexylaluminum is more preferable, and in particular, triisobutylaluminum or tri-n-hexylaluminum is preferable.

These organoaluminum compounds may be used alone, or in combination of two or more.

The ratio (molar ratio) of the amount used of the respective catalyst components in the present invention is not particularly limited, and the molar ratio of the component (A) to the component (B) is usually a molar ratio of a range of (A):(B)=from 1:1 to 10000:1, preferably from 1:1 to 5000:1, and more preferably a molar ratio of a range of from 1:1 to 1000:1. The amount used in case of using the component(C) is usually a molar ratio of a range of (B):(C) =from 0.1:1 to 1:10000, and preferably a molar ratio of a range of from 1:1 to 1:1000.

As the catalyst for addition polymerization of the present invention, a reaction product obtained by preliminarily contacting the component (A) and the component (B), optionally, further the component (C) may be also used, and they may be also used by being separately charged in a polymerization vessel. The arbitrary two components among them may be also previously contacted, and further, another component may be also contacted.

As monomers which can be used, any one of olefins having 2 to 100 carbon atoms, diolefins, cyclic olefins, alkenyl aromatic hydrocarbons and polar monomers can be used, and two or more monomers thereof can also be used, simultaneously. Specific examples thereof include olefins such as ethylene, propylene, 1-butene, 1-pentene, 4-methyl-1-pentene-1, 5-methyl-1-hexene, 1-hexene, 1-heptene, 1-octene, 1-nonene, 1-decene and vinylcyclohexane; diolefins such as 1,5-hexadiene, 1,4-hexadiene, 1,4-pentadiene, 1,7-octadiene, 1,8-nonadiene, 1,9-decadiene, 4-methyl-1,4-hexadiene, 5-methyl-1,4-hexadiene, 7-methyl-1,6-octadiene, 5-ethylidene-2-norbornene, dicyclopentadiene, 5-vinyl-2-norbornene, 5-methyl-2-norbornene, norbornadiene, 5-methylene-2-norbornene, 1,5-cyclooctadiene, 5,8-endomethylenehexahydronaphthalene, 1,3-butadiene, isoprene, 1,3-hexadiene, 1,3-octadiene, 1,3-cyclooctadiene and 1,3-cyclohexadiene; cyclic olefins such as norbornene, 5-methylnorbornene, 5-ethylnorbornene, 5-butylnorbornene, 5-phenylnorbornene, 5-benzylnorbornene, tetracyclododecene, tricyclodecene, tricycloundecene, pentacyclopentadecene, pentacyclohexadecene, 8-methyltetracyclododecene, 8-ethyltetracyclododecene, 5-acetylnorbornene, 5-acetyloxynorbornene, 5-methoxycarbonylnorbornene, 5-ethoxycarbonylnorbornene, 5-methyl-5-methoxycarbonylnorbornene, 5-cyanonorbornene, 8-methoxycarbonyltetracyclododecene, 8-methyl-8-tetracyclododecene and 8-cyanotetracyclododecene; alkenyl aromatic hydrocarbons such as alkenylbenzenes (e.g. styrene, 2-phenylpropylene, 2-phenylbutene, 3-phenylpropylene), alkylstyrenes (e.g. p-methylstyrene, m-methylstyrene, o-methylstyrene, p-ethylstyrene, m-ethylstyrene, o-ethylstyrene, 2,4-dimethylstyrene, 2,5-dimethylstyrene, 3,4-dimethylstyrene, 3,5-dimethylstyrene, 3-methyl-5-ethylstyrene, p-tert-butylstyrene and p-sec-butylstyrene), bis(alkenyl) benzenes (e.g. divinylbenzene) and alkenylnaphthalenes (e.g. 1-vinylnaphthalene); polar monomers such as α, β-unsaturated carboxylic acids (e.g. acrylic acid, methacrylic acid, fumaric acid, maleic anhydride, itaconic acid, itaconic anhydride, bicyclo(2,2,1)-5-heptene-2,3-dicarboxylic acid) and metal salts thereof (e.g. salts of sodium, potassium, lithium, zinc, magnesium and calcium), α, β-unsaturated carboxylic acid esters (e.g. methyl acrylate, ethyl acrylate, n-propyl acrylate, isopropyl acrylate, tert-butyl acrylate, 2-ethylhexyl acrylate, methyl methacrylate, ethyl methacrylate, n-propyl methacrylate, isopropyl methacrylate, n-butyl methacrylate, isobutyl methacrylate), unsaturated dicarboxylic acids (e.g. maleic acid, itaconic acid ), vinyl esters (e.g. vinyl acetate, vinyl propionate, vinyl capronate, vinyl caprate, vinyl laurate, vinyl stearate, vinyl trifluoroacetate), unsaturated carboxylic acid glycidylate (e.g. acrylic acid glycidylate, methacrylic acid glycidylate, itaconic acid monoglycidylate), cyclic ethers(e.g. ethylene oxide, propylene oxide, 1-hexene oxide, cyclohexene oxide, styrene oxide, tetrahydrofuran), and the like.

The catalyst for addition polymerization of the present invention can be applied to homopolymerzation or copolymerzation of these monomers. Examples of a combination of monomers constituting the copolymer include ethylene and propylene, ethylene and 1-butene, ethylene and 1-hexene and propylene and 1-butene, but the present invention should not be limited thereto.

The catalyst can be suitably applied to a process for producing an olefin polymer as a catalyst for olefin polymerization. The olefin polymer is preferably copolymers of ethylene with an α-olefin more preferably α-olefin having 3 to 20 carbon atoms obtained by copolymerising a mixture of ethylene with the α-olefin, and among these, linear low density polyethylene (LLDPE) is more preferred.

Concerning the polymerization method, it should not be specifically limited. For example, there are mentioned a solvent polymerization or a slurry polymerization in which an aliphatic hydrocarbon (e.g. butane, pentane, hexane, heptane, octane), an aromatic hydrocarbon (e.g. benzene, toluene) or a halogenated hydrocarbon (e.g. methylene dichloride) is used as a solvent, a bulk polymerization in which polymerization is carried out in a liquid monomer, a gas phase polymerization in which polymerization is carried out in a gaseous monomer, a high-pressure polymerization method in which polymerization is carried out in a supercritical liquid condition at a high temperature under a high pressure, etc. As polymerization form, either of a batch-wise type and a continuous type are possible.

The method of feeding the respective components in a reactor is not particularly limited. A method of feeding the respective components in a solid condition, or a method of feeding them in a condition of a solution in which they are dissolved in a hydrocarbon solvent from which components such as moisture, oxygen and the like deactivating catalyst components are removed, of a suspension or of a slurry, is mentioned.

When the respective components are used as a solution, the concentration of the component (A) and the component (C) are usually 0.0001 to 100 mmol/L converted to metal atom, and preferably 0.01 to 10 mmol/L, respectively. The concentration of the component (B) is usually 0.0001 to 100 mmol/L converted to metal atom, and preferably 0. 01 to 10 mmol/L.

The polymerization temperature is usually from −100° C. to 350° C., preferably from −20° C. to 300° C., and more preferably from 160° C. to 300° C. The polymerization pressure is usually from 0.1 to 350 MPa, preferably from 0.1 to 300 MPa, and more preferably from 0.1 to 200 MPa. In general, the polymerization time can be appropriately determined according to the kind of a desired polymer and a reaction apparatus, and a range of form 1 minute to 20 hours can be adopted.

In order to control the molecular weight of a polymer, a chain transfer agent such as hydrogen or the like may be added.

EXAMPLE

The present invention is further illustrated in detail according to Examples and Comparative Examples below, but the present invention is not limited thereto.

The measurement values of respective items in Examples were measured according to methods described below.

(1) Content of α-olefin Unit in Copolymer (Short Chain Branch Degree)

The content of α-olefin units (Short chain branch degree) in a copolymer was determined from IR absorption spectrum. In addition, the measurement and calculation were carried out by using characteristic absorptions derived from the α-olefin according to a method described in "Die Makromoleculare Chemie, 177, 449(1976) McRae, M. A., Madams, W. F.". and the IR absorption spectrum was obtained by a measurerent using an infrared spectrometer (FT-IR7300, manufactured by NIPPON BUNKO Inc.). The short-chain branch degree was represented as a short-chain branch (SCB) number per 1000 carbon atoms.

(2) Intrinsic Viscosity ([η]):

It was measured at 135° C. in a tetralin solution using an Ubbelohde viscometer.

(3) Measurement of $^{13}$C-NMR

JNM-EX270 (67.5MHz, $^{13}$C) (manufactured by JEOL LTD.) was used for measuring $^{13}$C-NMR. A deuterated solvent described in Example was used and the measurement was carried out at room temperature.

(4) Molecular Weight and Molecular Weight Distribution:

They were determined under the under-mentioned conditions according to a gel permeation chromatography (GPC). Calibration curve was prepared using a standard polystyrene. Molecular weight distribution was evaluated by a ratio (Mw/Mn) of weight average molecular weight (Mw) to number average molecular weight (Mn).
Equipment: 150C type, manufactured by Milipore Waters Co., Ltd.
Column: TSK-GEL GMH-HT; (7.5 mmφ×600 mm) 2 columns
Measurement temperature: 140° C.
Solvent: o-dichlorobenzene
Measurement concentration: 5 mg/5 ml (5) Melting Point It was measured under the following conditions by using Seiko SSC-5200.
Heating: heating from 40 to 150° C. (10° C./min.) and maintaining for 5 minutes at 150° C.
Cooling: cooling from 150 to 10° C. (5° C./min.) and maintaining for 10 minutes at 10° C. after Heating
Measurement: measured by immediately heating from 10 to 160° C. (5° C./min.) after Cooling

Example 1

(1) Preparation of Compound(A)

Into a 500 ml four-necked flask in which the atmosphere was replaced with argon, 29.6 g (67.3 mmol) of triphenyl bismuth and 100 ml of toluene were charged. Thereto, 75.3 ml (209 mmol) of pentafluorophenol (2.77M, toluene solution) was added dropwise at room temperature. After completion of dropwise addition, 150 ml of toluene was added thereto. Stirring was carried out for 12 hours under a refluxing condition. A yellow crystal formed by allowing to stand at room temperature was collected by filteration, then dried under reduced pressure to obtain 46.1 g of the yellow crystal. As a result of an elementary analysis, Bi=1.2 mmol/g, F=17 mmol/g and C=25 mmol/g.

Into a 100 ml four-necked flask in which the atmosphere was replaced with argon, 0.991 g (1.19 mmol-Bi) of the yellow crystal and 20 ml of toluene were charged. Thereto, 4.2 μml (0.23 mmol) of H$_2$O was added at room temperature, then the resultant was stirred for 1 hour at 80° C. to obtain a slurry (herein-after, referred to as "Compound(A1) slurry". The concentration of compound(Al) in the slurry was determined as 58.3 μmol-Bi/ml by calculation from the amount of the slurry.

(2) Preparation of Transition Metal Compound: dimethylsilylene(η$^5$-tetramethylcyclopentadienyl) (3-tert-butyl-5-methyl-2-phenoxy)titanium dimethoxide)(Compound B1)

In a Schlenk tube, 0.131 g (4.1 mmol) of methyl alcohol was dissolved in 10 ml of anhydrous diethyl ether and a diethyl ether solution (3.9 ml, 4.1 mmol) of methyllithium having a concentration of 1.05 mol/L was added dropwise at −78° C. thereto. The resulting mixture was heated to 20° C., the formation of lithium methoxide was confirmed by gas generation, and the resulting reaction solution was again cooled to −78° C. Into the reaction solution, 20 ml of an anhydrous diethyl ether suspension liquid of 0.919 g (2.0 mmol) of dimethylsilylene(η$^5$-tetramethylcyclopentadienyl) (3-tert-butyl-5-methyl-2-phenoxy)titanium dichloride which was previously prepared in another Schlenk tube was transferred, and then, the resulting reaction mixture was gradually heated to room temperature to obtain a reaction solution. After concentrating the reaction solution, 20 ml of toluene was added and an insoluble product was separated by filtration. The filtrate was concentrated to obtain dimethylsilylene(η$^5$-tetramethylcyclopentadienyl)(3-tert-butyl-5-methyl-2-phenoxy)titanium dimethoxide represented by the structural formula described below of yellow crystals (0.86 g, 95%).

$^1$H-NMR (270 MHz, C$_6$D$_6$); δ7.26 (m, 2H), 4.13(s, 6H), 2.33 (s, 3H), 1.97(s, 6H), 1.89(s, 6H), 1.59(s, 9H), 0.55(s, 6H)

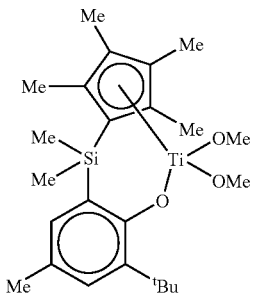

(3) Production of Addition Polymer

After drying under vacuum an autoclave reactor having an inner volume of 400 ml equipped with a stirrer and replacing the atmosphere thereof with argon, 185 ml of cyclohexane as a solvent and 15 ml of 1-hexene as a comonomer were charged and the reactor was heated to 180° C. After the raise of temperature, ethylene was fed while adjusting at an ethylene pressure of 2.5 MPa. After the system was stabilized, 0.3 ml(300 μm) of triisobutylaluminum (1 mmol/ml, toluene solution) was charged, successively, a heptane solution in which the compound B1 and triisobutylaluminum were mixed (concentration of B1; 1 μmol, concentration of triisobutylaluminum; 50 μmol, molar ratio of Al atom to Ti atom ;50)(Namely, B1 is 0.5 mmol, and triisobutylaluminum is 25 μmol) was charged, further, 4.3 ml of Compound Al slurry(250 μmol/Bi) was charged to initiate polymerization.

The polymerization was carried out 2 minutes. As polymerization results, 0.04 g of an ethylene-1-hxene copolymer was obtained. Further, a polymerization activity was $8.0 \times 10^4$ g/mol-Ti/2 minutes, Mw was 120,000, and Mw/Mn was 1.7.

Example 2

(1) Preparation of Compound(A)

Synthesis of the compound (A) of Example 1 was repeated except that 0.983 g(1.18 mmol-Bi) of the yellow crystal and 10.4 μl(0.577 mmol) of $H_2O$ were used, to obtain a slurry (herein after, referred to as "Compound A2 slurry"). The concentration of compound(A1) in the slurry was determined as 57.8 μmol-Bi/ml by calculation from the amount of the slurry.

(2) Production of Addition Polymer

Production of addition polymer in Example 1 was repeated except that 4.3 ml(250 mmol-Bi) of Compound A2 slurry was used instead of Compound A1 slurry.

As polymerization results, 0.30 g of an ethylene-1-hxene copolymer was obtained. Further, a polymerization activity was $6.0 \times 10^5$ g/mol-Ti/2 minutes, Mw was 130,000, [η] was 1.94 dl/g, Mw/Mn was 1.7, and SCB was 29.5.

Example 3

(1) Preparation of Compound(A)

Synthesis of the compound (A) of Example 1 was repeated except that 1.05 g(1.26 mmol-Bi) of the yellow crystal and 15.6 μl (0.866 mmol) of $H_2O$ were used, to obtain a slurry (herein after, referred to as "Compound A3 slurry"). The concentration of compound(A1) in the slurry was determined as 61.7 μmol-Bi/ml by calculation from the amount of the slurry.

(2) Production of Addition Polymer

Production of addition polymer in Example 1 was repeated except that 4.1 ml(250 mmol-Bi) of Compound A3 slurry was used instead of Compound A1 slurry.

As polymerization results, 0.64 g of an ethylene-1-hxene copolymer was obtained. Further, a polymerization activity was $1.3 \times 10^6$ g/mol-Ti/2 minutes, Mw was 120,000, [η] was 1.93 dl/g, Mw/Mn was 1.8, SCB was 30.2, and Mp was 86.5° C.

Example 4

(1) Preparation of Compound(A)

Synthesis of the compound (A) of Example 1 was repeated except that 1.03 g(1.24 mmol-Bi) of the yellow crystal and 21.8 μl (1.21 mmol) of $H_2O$ were used, to obtain a slurry (herein after, referred to as "Compound A4 slurry"). The concentration of compound(A1) in the slurry was determined as 60.6 μmol-Bi/ml by calculation from the amount of the slurry.

(2) Production of Addition Polymer

Production of addition polymer in Example 1 was repeated except that 4.1 ml(250 mmol-Bi) of Compound A4 slurry was used instead of Compound A1 slurry.

As polymerization results, 2.05 g of an ethylene-1-hxene copolymer was obtained. Further, a polymerization activity was $4.1 \times 10^6$ g/mol-Ti/2 minutes, Mw was 120,000, [η] was 1.81 dl/g, Mw/Mn was 1.7, SCB was 29.5, and Mp was 89.3° C.

Example 5

(1) Preparation of Compound(A)

Synthesis of the compound (A) of Example 1 was repeated except that 0.913 g(1.10 mmol-Bi) of the yellow crystal and 23.2 μl(1.29 mmol) of $H_2O$ were used, to obtain a slurry (herein after, referred to as "Compound A5 slurry"). The concentration of compound(A1) in the slurry was determined as 53.7 μmol-Bi/ml by calculation from the amount of the slurry.

(2) Production of Addition Polymer

Production of addition polymer in Example 1 was repeated except that 4.7 ml(250 mmol-Bi) of Compound A5 slurry was used instead of Compound A1 slurry.

As polymerization results, 1.98 g of an ethylene-1-hxene copolymer was obtained. Further, a polymerization activity was $4.0 \times 10^6$ g/mol-Ti/2 minutes.

Example 6

(1) Preparation of Compound(A)

Synthesis of the compound (A) of Example 1 was repeated except that 1.02 g(1.21 mmol-Bi) of the yellow crystal and 32.6 μl(1.81 mmol) of $H_2O$ were used, to obtain a slurry (herein after, referred to as "Compound A6 slurry"). The concentration of compound(A1) in the slurry was determined as 60.3 μmol-Bi/ml by calculation from the amount of the slurry.

(2) Production of Addition Polymer

Production of addition polymer in Example 1 was repeated except that 4.1 ml(250 mmol-Bi) of Compound A6 slurry was used instead of Compound A1 slurry.

As polymerization results, 1.33 g of an ethylene-1-hxene copolymer was obtained. Further, a polymerization activity was $2.7 \times 10^6$ g/mol-Ti/2 minutes and Mw was 100000.

Example 7

(1) Preparation of Compound(A)

Into a 5 L four-necked flask in which the atmosphere was replaced with argon, 255 g (579 mmol) of triphenyl bismuth and 1.6 L of toluene were charged. Thereto, 653 ml (1.82 mol) of pentafluorophenol (2.79M, toluene solution) was added dropwise at room temperature. Stirring was carried out for 12 hours under a refluxing condition. A yellow crystal precipitated by allowing to stand at room temperature was collected by filtration, then dried under reduced pressure to obtain 447 g of the yellow crystal.

Into a 2 L four-necked flask replaced with argon, 178 g of the yellow crystal and 1.0 L of toluene were charged. The resulting mixture was stirred for 25 minutes at 80° C. to perfectly dissolve the yellow crystal in toluene. Next, 4.2 ml(233 mmol) of $H_2O$ was added dropwise thereto over 25 minutes. After the dropping, the resultant was stirred for one hour at 80° C. to precipitate a white powder. After cooled to room temperature, the resulted mixture was allowed to stand to precipitate a solid formed, and the supernatant liquid was taken out. The solid was washed with 500 ml of toluene, then twice with each 500 ml of hexane and dried under reduce pressure to obtain 99.0 g of a white compound (referred to as "Compound A7").

(2) Production of Addition Polymer

After drying under vacuum an autoclave reactor having an inner volume of 400 ml equipped with a stirrer and replacing the atmosphere thereof with argon, 185 ml of toluene as a solvent and 15 ml of 1-hexene as a comonomer were charged and the reactor was heated to 180° C. After the raise of temperature, ethylene was fed while adjusting at an ethylene pressure of 2.5 MPa. After the system was stabilized, 0.3 ml(300 µmol) of triisobutylaluminum (1 mmol/ml, toluene solution) was charged, successively, a heptane solution in which the compound B1 and triisobutylaluminum were mixed (concentration of B1; 1 µmol, concentration of triisobutylaluminum: 50 µmol, molar ratio of Al atom to Ti atom; 50)(Namely, B1 is 0.5 mmol, and triisobutylaluminum is 25 mol) was charged, further, 5.0 ml of a slurry of 4.98 wt. % of the compound A7 was charged to initiate polymerization.

The polymerization was carried out 2 minutes. As polymerization results, 0.86 g of an ethylene-1-hexene copolymer was obtained. Further, a polymerization activity was $1.7 \times 10^6$ g/mol-Ti/2 minutes, [η] was 2.08 dl/g, Mw was 160,000, Mw/Mn was 1.8, SCB was 25 and melting point was 92.7° C.

Comparative Example 1

(1) Production of Addition Polymer

Production of addition polymer in Example 1 was repeated except that 50 mmol-Bi of the yellow crystal obtained in Preparation of compound A was used instead of Compound A1 slurry.

As polymerization results, only a trace amount of an ethylene-1-hxene copolymer could be obtained.

Comparative Example 2

(1) Preparation of Zinc Compound

Into a 5-liter four-necked flask in which the atmosphere was replaced with nitrogen, 1.5 liters of tetrahydrofuran, and 1.35 liters of a hexane solution of $ZnEt_2$(concentration: 2.0 mol/l, amount: 2.75 mol) were charged, and cooled to 5° C. in an ice bath. A solution in which 203.3 g (1.1 mol) of pentafluorophenol was dissolved with 300 ml of tetrahydrofuran, was added dropwise thereto. After completion of dropping, the resultant was stirred at 5° C. for 1 hour, thereafter, was heated to 45° C. and stirred additionally 1 hour. After cooled to 20° C., 45.2 g (2.51 mol) of $H_2O$ was added dropwise to the resultant.

Contents of the flask got cloudy. After completion of the dropwise, the contents was stirred for additional 1 hour, then heated to 45° C. and stirred for 1 hour. After allowed to stand at room temperature over night, tetrahydrofuran was distilled off under reduced pressure, then the residues were dried at 120° C. for 8 hours under reduced pressure to obtain 430.0 g of yellow powder. As an elementary analysis, contents of Zn and F were respectively 6.42 mmol/g and 13.7 mmol/g.

(2) Production of Addition Polymer

Example 1(3) was repeated except that 58.5 mg (376 µmol) of the zinc compound prepared in (1) above was used instead of the Compound A1 slurry. As polymerization results, only a trace amount of an ethylene-1-hxene copolymer could be obtained.

Comparative Example 3

Example 1(3) was repeated except that 3 µmol of N,N-dimethylaniliniumtetrakis(pentafluorophenyl)borate was used Instead of the Compound A1 slurry. As polymerization results, As polymerization results, 2.18 g of an ethylene-1-hxene copolymer was obtained. Further, a polymerization activity was $4.4 \times 10^6$ g/mol-Ti/2 minutes, [η] was 0.97 dl/g, Mw was 57,000, Mw/Mn was 2.0, and SCB was 33.6.

According to the present invention, a catalyst component for addition polymerization which can produce an addition polymer of high molecular weight, a catalyst for addition polymerization which is made by using the catalyst component, and a process for producing an addition polymer using the catalyst for addition polymerization can be provided. Further, the catalyst for addition polymerization of the present invention exhits a high polymerization activity, therefore, is fovorable for production of addition polymers.

The invention claimed is:

1. A catalyst component obtained by a process comprising contacting triphenyl bismuth, pentafluorophenol and water.

2. The catalyst component according to claim 1, wherein pentafluorophenol and water are contacted in amounts of 2.1 to 3.9 mol and 0.1 to 2 mol, respectively, per 1 mol of triphenyl bismuth.

3. A catalyst for addition polymerization prepared by a process comprising contacting:
   (A) a catlyst component obtained by a process comprising contacting triphenyl bismuth, pentafluorophenol and water, and
   (B) a compound of a metal selected from the group consisting of metals of Groups 3 to 11 and lanthanide series of the Periodic Table of the Elements.

4. A catalyst for addition polymerization prepared by a process comprising contacting:
   (A) a catalyst component obtained by a process comprising contacting bismuth, pentafluorophenol and water,
   (B) a compound of a metal selected from the group consisting of metals of Groups 3 to 11 and lanthanide series of the Periodic Table of the Elements, and
   (C) an organoaluminum compound.

5. The catalyst according to claim 3, wherein the compound (B) is a metallocene compound.

6. The catalyst according to claim 4, wherein the compound (B) is a metallocene compound.

7. The catalyst according to claim 5, wherein the metallocene compound is a monocyclopentadienyl metallic compound.

8. The catalyst according to claim 6, wherein the metallocene compound is a monocyclopentadienyl metallic compound.

9. The catalyst according to claim 7, wherein the monocyclopentadienyl metallic compound is any one of those represented by the chemical formulae [4] to [6] below:

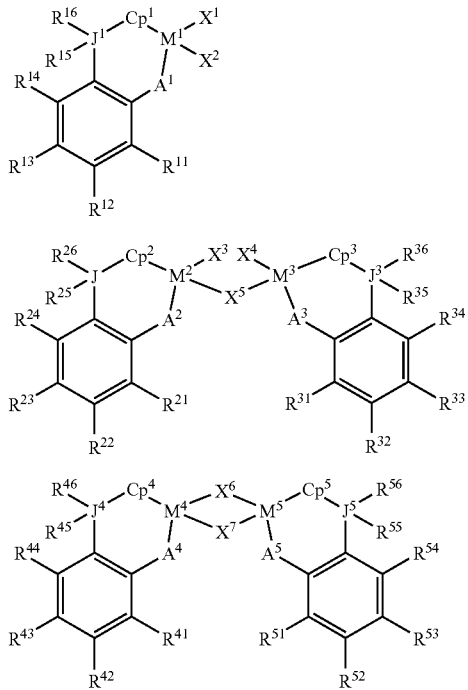

wherein $M^1$ to $M^5$ represent independently an atom of Group 4 of the periodic table of the elements; A1 to A5 represent independently an atom of Group 16 of the periodic table of the elements; J1 to J5 represent independently an atom of Group 14 of the periodic table of the elements; Cp1 to Cp5 represent a group having a cyclopentadienyl anion skeleton; $X^1$ to $X^5$, $R^{11}$ to $R^{16}$, $R^{21}$ to $R^{26}$, $R^{31}$ to $R^{36}$, $R^{41}$ to $R^{46}$ and $R^{51}$ to $R^{56}$ represent independently a hydrogen atom, a halogen atom, a hydrocarbon group, substituted silyl group, a hydrocarbonoxy group, di-substituted amino group, a hydrocarbon thio group or a hydrocarbon seleno group, wherein $R^{11}$ to $R^{16}$, $R^{21}$ to $R^{26}$, $R^{31}$ to $R^{36}$, $R^{41}$ to $R^{46}$ and $R^{51}$ to $R^{56}$ may link to form a single ring or a plurality of rings which may be aromatic ring(s) or non-aromatic ring(s); and $X^5$ to $X^7$ represent independently an atom of Group 16 of the periodic table of the elements.

10. The catalyst according to claim 8, wherein the monocyclopentadienyl metallic compound is any one of those represented by the chemical formulae [4] to [6] below:

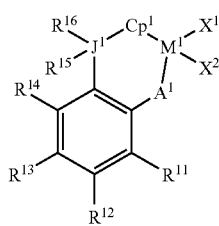

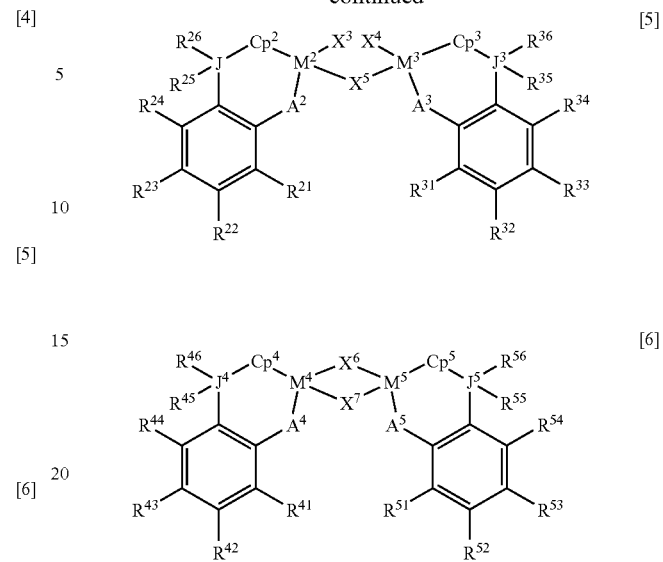

wherein $M^1$ to $M^5$ represent independently an atom of Group 4 of the periodic table of the elements; A1 to A5 represent independently an atom of Group 16 of the periodic table of the elements; J1 to J5 represent independently an atom of Group 14 of the periodic table of the elements; Cp1 to Cp5 represent a group having a cyclopentadienyl anion skeleton; $X^1$ to $X^5$, $R^{11}$ to $R^{16}$, $R^{21}$ to $R^{26}$, $R^{31}$ to $R^{36}$, $R^{41}$ to $R^{46}$ and $R^{51}$ to $R^{56}$ represent independently a hydrogen atom, a halogen atom, a hydrocarbon group, substituted silyl group, a hydrocarbonoxy group, di-substituted amino group, a hydrocarbon thio group or a hydrocarbon seleno group, $R^{11}$ to $R^{16}$, $R^{21}$ to $R^{26}$, $R^{31}$ to $R^{36}$, $R^{41}$ to $R^{46}$ and $R^{51}$ to $R^{56}$ may link to form a single ring or a plurality of rings which may be aromatic ring(s) or non-aromatic ring(s); and $X^5$ to $X^7$ represent independently an atom of Group 16 of the periodic table of the elements.

11. A process for producing an addition polymer which comprises polymerizing an addition polymerizable monomer with the catalyst of claim 3.

12. A process for producing an addition polymer which comprises polymerizing an addition polymerizable monomer with the catalyst of claim 4.

13. The process according to claim 11, wherein the addition polymerizable monomer is an olefin.

14. The process according to claim 12, wherein the addition polymerizable monomer is an olefin.

15. The process according to claim 13, wherein the olefin is a mixture of ethylene with an α-olefin having 3 to 20 carbon atoms.

16. The process according to claim 14, wherein the olefin is a mixture of ethylene with an α-olefin having 3 to 20 carbon atoms.

* * * * *